US008187610B2

(12) United States Patent
Waller et al.

(10) Patent No.: US 8,187,610 B2
(45) Date of Patent: May 29, 2012

(54) *STREPTOCOCCUS EQUI* STRAIN

(75) Inventors: Andrew Stephen Waller, Suffolk (GB); Carl Robinson, Suffolk (GB); Zoe Heather, Victoria (GB)

(73) Assignee: Animal Health Trust, Suffolk (GB)

( * ) Notice: Subject to any disclaimer, the term of this patent is extended or adjusted under 35 U.S.C. 154(b) by 0 days.

(21) Appl. No.: 12/864,034

(22) PCT Filed: Jan. 20, 2009

(86) PCT No.: PCT/GB2009/000155
§ 371 (c)(1),
(2), (4) Date: Jul. 22, 2010

(87) PCT Pub. No.: WO2009/093014
PCT Pub. Date: Jul. 30, 2009

(65) Prior Publication Data

US 2010/0297184 A1 Nov. 25, 2010

(30) Foreign Application Priority Data

Jan. 24, 2008 (GB) .................................. 0801326.0

(51) Int. Cl.

| | |
|---|---|
| ***A61K 39/09*** | (2006.01) |
| ***C12N 1/21*** | (2006.01) |
| ***C12N 15/00*** | (2006.01) |
| ***A61P 37/04*** | (2006.01) |
| ***A61P 31/04*** | (2006.01) |

(52) U.S. Cl. ............... 424/244.1; 424/231.1; 435/252.3; 435/44; 435/243; 435/253.4

(58) Field of Classification Search ........................ None
See application file for complete search history.

(56) References Cited

U.S. PATENT DOCUMENTS

2006/0110411 A1 5/2006 Chu

FOREIGN PATENT DOCUMENTS

| | | |
|---|---|---|
| EP | 0786518 A | 7/1997 |
| EP | 1023903 A | 8/2000 |
| WO | 03/046183 A | 6/2003 |

OTHER PUBLICATIONS

Greenspan et al. (Nature Biotechnology 7: 936-937, 1999).*
Roche et al., "Live Attenuated *Streptococcus pneumoniae* Strains Induce Serotype-Independent Mucosal and Systemic Protection in Mice", Infection and Immunity, vol. 75, No. 5, May 2007, pp. 2469-2475.
Betschel, et al., "Reduced Virulence of Group A Streptococcal Tn916 Mutants That Do Not Produce Streptolysin S", Infection and Immunity, American Society for Microbiology, Washington, US, vol. 66, No. 4, Apr. 1, 1998, pp. 1671-1679.
Walker: et al., "Construction of a Stable Non-Mucoid Deletion Mutant of the *Streptococcus equi* Pinnacle Vaccine Strain", Veterinary Microbiology, Vol. 89, No. 4, Nov. 6, 2002, pp. 311-321.
Kelly et al., "Sequence Variation of the SeM Gene of *Streptococcus equi* Allows Discrimination of the Source of Strangles Outbreaks", Journal of Clinical Microbiology, Feb. 2006, vol. 44, No. 2, Feb. 2006, pp. 480-486.
Hamilton et al., "Mutation of the Maturase Lipoprotein Attenuates the Virulence of *Streptococcus equi* to a Greater Extent than Does Loss of General Lipoprotein Lipidation", Infection and Immunity, vol. 74, No. 12, Dec. 2006, pp. 6907-6919.
Waller et al., "Vaccination of Horses Against Strangles Using Recombinant Antigens from *Streptococcus equi*", Vaccine, Butterworth Scientific, Guildford, GB, vol. 25, No. 18, Apr. 17, 2007, pp. 3629-3625.
Kemp-Symonds, et al., "Modified Live *Streptococcus equi* ('strangles') Vaccination Followed by Clinically Adverse Reactions Associated with Bacterial Replication", Equine Veterinary Journal, vol. 39, No. 3, May 2007, pp. 284-286.
Flanagan et al., "Characterizaton of the Haemolytic Activity of *Steptococcus Equi*", Microbial Pathogenesis, vol. 24, No. 4, Apr. 1998, pp. 211-221.
Waller, et al., "Getting a Grip on Strangles: Recent Progress Towards Improved Diagnostics and Vaccines", Veterinary Journal, Baillier Tindall, London, GB, vol. 173, No. 3, May 1, 2007, pp. 492-501.

* cited by examiner

*Primary Examiner* — Robert A Zeman
(74) *Attorney, Agent, or Firm* — Kilpatrick Townsend & Stockton LLP

(57) ABSTRACT

The invention provides *Streptococcus* vaccine strains (e.g. *S. equi* which is causative of 'strangles') comprising the following modifications in their genomes: (i) attenuation of one or more essential biosynthetic genes, (ii) attenuation of one or more genes which encode a haemolytic toxin, or protein involved in the production thereof, plus preferably any one, two, or most preferably three of the following modifications: (iii) attenuation of one or more genes which encode a protein responsible for immune evasion (iv) modification of one or more genes such as to permit serological discrimination of the vaccine strain based on analysis of a protein encoded by said genes, and (v) attenuation of one or more genes which encode an enzyme responsible for recombination repair of the genome. The invention provides inter alia live attenuated vaccine strains which generate an immune response to multiple protective epitopes presented in a context resembling the live pathogen.

2 Claims, 3 Drawing Sheets

*STREPTOCOCCUS EQUI* STRAIN

CROSS REFERENCE TO RELATED APPLICATIONS

Figure 1:
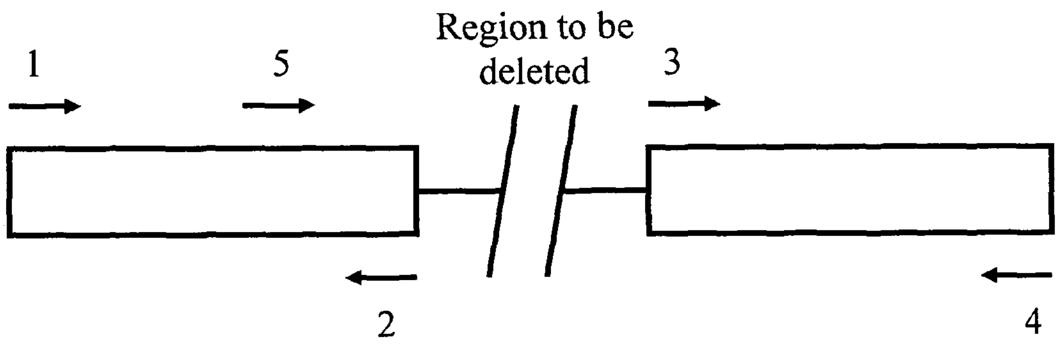

This application is the U.S. National Phase of PCT/GB2009/000155 filed on Jan. 20, 2009 which claims the benefit British Application No. 0801326.0 filed on Jan. 24, 2008, both of which are incorporated herein by reference.

TECHNICAL FIELD

The present invention relates generally to methods and materials concerning diseases caused by Streptococcal pathogens, and in particular relating to attenuated strains of Streptococci and use of the same as vaccines.

Microorganism Deposit

A micro-organism deposit in accordance with the Budapest treaty has been at the National Collection of Type Cultures (NCTC), Health Protection Agency, Centre for Infections 61, Colindale Avenue, LONDON NW9 5EQ, United Kingdom under accession number: 13412 on date 26 Sep. 2007 on behalf of the present applicant by the present inventors.

The depositors have authorised the present applicant to refer to the deposited biological material in the application.

BACKGROUND ART

*Streptococcus* is a genus of spherical shaped Gram-positive bacteria. Clinically, individual species of *Streptococcus* are classified primarily based on their Lancefield serotyping—according to specific carbohydrates in the bacterial cell wall. These are named Lancefield groups A to T. However the pathogens in these different groups share many similarities at the genetic level. For example *Streptococcus equi* (which is in group C, and which is the causative agent of equine strangles) shares 80% genome identity with the human pathogen *S. pyogenes* (which is in group A, and which is the causative agent of many human conditions including strep throat, acute rheumatic fever, scarlet fever, acute glomerulonephritis and necrotizing fasciitis). Additionally the two organisms share many near identical toxins and virulence factors.

Streptococci are further characterised via their haemolytic properties. Alpha haemolysis is caused by a reduction of iron in haemoglobin giving it a greenish color on blood agar. Beta only haemolysis is complete rupture of red blood cells giving distinct, wide, clear areas around bacterial colonies on blood agar. Other streptococci are labeled as gamma haemolytic.

Strangles is a disease characterised by nasal discharge and fever, followed by abscessation of local lymph nodes. The swelling of the lymph nodes in the head and neck may, in severe cases, restrict the airway and it is this clinical feature that gave the disease 'strangles' its name. Morbidity rates of up to 100% are reported and mortality as a result of disseminated abscessation ('bastard strangles') may occur in 10% of cases (Timoney, 1993a). Strangles is one of the most frequently diagnosed equine diseases worldwide. Recent outbreaks in Thoroughbreds have further highlighted the need for the development of improved therapies. Antibiotic treatment is usually ineffective despite *S. equi's* susceptibility to most antibiotics in vitro. Clinical signs following treatment have been reported to abate only until treatment is withdrawn. This relapse is probably due to the lack of sufficient vascularity in the abscess to enable antibiotic penetration to therapeutic levels and illustrates the importance of the development of an effective preventative vaccine (Harrington et al., 2002). Approximately 10% of horses that recover from strangles become carriers of the disease, harbouring the infectious agent in chondroids located in the guttural pouch. These carriers are capable of infecting other naïve horses and continue the spread of disease (Chanter et al., 2000, Newton et al., 1997, Newton et al., 2000). Therefore, a major goal of vaccine design is not only to protect against strangles, but also to prevent development of the carrier state.

Progress in the development of an effective strangles vaccine has been slow. Vaccines against the disease have been known for a long time (Bazeley, 1940 and Bazeley, 1942), but have either proved ineffective or suffer from undesirable side effects.

Four kinds of vaccines are available: a) vaccines based on classical bacterins, b) sub-unit vaccines based on the M-protein, an immunogenic protein, c) Chemically attenuated live *Streptococcus equi* and d) Genetically attenuated live *Streptococcus equi*.

Conventional vaccines containing inactivated whole bacteria or extracts have shown little efficacy and often induce adverse reactions (Jorm, 1990, Timoney and Eggers, 1985). Classical vaccines based on bacterins or subunits are e.g. available through Fort Dodge Laboratories and Coopers Animal Health.

Those vaccines that specifically target the M-protein of *S. equi*, showed promise in mouse vaccination challenge studies (Meehan et al., 1998), but failed to demonstrate significant protection in horses despite the generation of M-protein reactive antibodies (Timoney et al., 1997, Sheoran et al., 2002).

Similarly, a recombinant *S. equi* hyaluronate associated protein (HAP) vaccine, was partially protective in mice (Chanter et al., 1999), but failed to prevent the development of strangles in vaccinated horses (N. Chanter unpublished results).

The basis and duration of protective immunity following natural infection is not fully understood, but in the majority of animals that recover from strangles immunity is believed to last for >5 years (Hamlen et al., 1994; Sweeney et al., 2005; Todd 1910; Woolcock, 1975).

A non-specifically attenuated vaccine strain for intranasal inoculation, the 'Pinnacle I.N.' strangles vaccine, is marketed by Fort Dodge (Timoney, 1993b). This acapsular strain was derived following chemical mutagenesis to induce random mutations throughout the bacterial genome (Timoney, 1993b). Such non-defined point mutations are prone to back mutation and thus to reversion to full virulence and although this vaccine may protect up to 100% of horses (Timoney, 1993b, Walker and Timoney 2002), it has not been licensed for sale in Europe due to safety concerns. These include nasal discharge, lymphadenectasis and a 5% risk of submandibular abscesses following IN vaccination (Timoney, 1993b). US2006110411 (WYETH FORT DODGE LAB (US)) relates to compositions comprising live, attenuated *S. equi*.

Recently, an Intervet live attenuated vaccine strain TW 928 has been approved for sale in Europe, marketed as 'Equilis StrepE'. This strain was attenuated by the partial deletion of the aroA gene and was $10^4$-fold attenuated during intraperitoneal mouse challenge studies (Hartford et al., 1999). The TW 928 vaccine strain was attenuated in six horses with no signs of disease apparent at post mortem examination four weeks after intranasal challenge (Hartford et al., 1999). Intramuscular vaccination of horses with strain TW 928 conferred 100% protection from subsequent *S. equi* challenge. However, severe injection site reactions precluded the use of this route for future studies. Further, contamination of needles to be used for the administration of other products with the Equilis StrepE vaccine have also led to abscess formation at the intramuscular injection site (Kemp-Symonds et al., 2007).

In order to minimise injection site reactions and retain some protective efficacy, sub-mucosal vaccination with $10^9$ cfu of the TW 928 strain into the inside of the upper lip was evaluated. Using this method, small pustules formed over a period of one week from which the TW 928 strain could be isolated. Horses were 50% protected from intranasal *S. equi* challenge and a further 25% of vaccinates had reduced clinical signs of disease. The presence of these pustules may be critical for the generation of an efficacious immune response since on dose reduction reduced injection site reactions correlated with decreased protection (Jacobs et al., 2000).

We have also observed cases of sub-mandibular lymph node abscessation in horses recently vaccinated with Equilis StrepE. In three of these cases we have confirmed by genetic analysis that the causal agent was the vaccine strain (Kemp-Symonds et al., 2007; Waller et al., unpublished data).

In addition, an undetermined proportion of the 25% of vaccinated horses, which on exposure to virulent *S. equi* suffer reduced clinical signs may go on to become carriers of virulent field strains of *S. equi* without being diagnosed. Such a scenario is of major concern to disease prevention strategies.

Finally, the vaccine suffers from only a 3-month duration of immunity, although boosting of horses vaccinated up to six months previously in the face of an outbreak has been shown to improve clinical outcome and extends the usefulness of this vaccine.

Overall, 'Equilis StrepE' is a promising advance over the Pinnacle strain (most notably in its lower risk of reversion). However, it is only recommended for use in horses of high or moderate risk of strangles where acquisition of a short duration of immunity is advantageous. Additionally, it suffers a number of drawbacks as discussed above.

It will be appreciated that novel vaccine strains which could overcome one or preferably more than one of these drawbacks would provide a contribution to the art.

DISCLOSURE OF THE INVENTION

The present inventors have considered the drawbacks in the prior art above and have determined that greatest protection against Streptococcal pathogens may be achieved by use of preferably live attenuated strains which generate an immune response to multiple protective epitopes presented in a context most resembling the live pathogen.

Such strains are provided herein.

In respect of strangles vaccines, the attenuated vaccines described herein may offer improved efficacy, intramuscular safety, have a generally improved safety profile, and may not cause the occasional lymph node abscessation found with the prior art.

In one embodiment there is disclosed herein

A *Streptococcus* vaccine strain comprising the following modifications in its genome:

(i) attenuation of one or more essential biosynthetic genes, (ii) attenuation of one or more genes which encode a haemolytic toxin, or a protein involved in the production thereof, plus preferably any one, two, or most preferably three of the following modifications:

(iii) attenuation of one or more genes which encode a protein responsible for immune evasion, (iv) modification of one or more genes such as to permit serological discrimination of the vaccine strain based on analysis of a protein encoded by said genes, and (v) attenuation of one or more genes which encode an enzyme responsible for recombination repair of the genome.

By "attenuation" is meant modification of the sequence of relevant gene and hence impairment of the function or activity of the encoded protein. Preferred attenuations are deletion of all or part of the gene, or the introduction of substitutions therein. Preferably attenuation is achieved by at least one well-defined irreversible deletion of substantial size.

Those skilled in the art will appreciate that the strains of the present invention may combine one or more further attenuations in addition to those described above.

Some particular aspects and embodiments of the invention will now be discussed in more detail.

Biosynthetic Genes

The inventors have determined that attenuation of *S. equi* TW 928 by the deletion of only one gene may not remove the possibility of strain reversion. Acquisition of homologous DNA from the commensal *S. zooepidemicus* followed by recombination and repair of the TW 928 genome remains a small, but unknown risk factor in the use of this strain in equids.

Preferably therefore two essential biosynthetic genes are attenuated. Preferably the genes are partially or fully deleted.

Preferred target biosynthetic genes are those in the aromatic or pyramidine (or purine) pathways. Preferred genes are aroB and pyrC.

Deletion of genes in the aromatic amino acid biosynthetic pathway is known to attenuate pathogens and has been used to generate the TW 928 *S. equi* strain and several non-streptococcal vaccine strains (Ingham et al., 2002, Simmons et al., 1997, Chamberlain et al., 1993, Alexander et al., 1993, Vaughan et al., 1993, Karnell et al., 1992, Newland et al., 1992, Stocker 1990, Izhar et al., 1990).

Purine and pyrimidine biosynthesis have been targets for attenuation of pathogenic *E. coli* (Kwaga et al., 1994) and inactivation of pyrC is known to prevent growth of *B. subtilis* in minimal media (Waller et al., 2001).

Haemolytic Toxin

As noted above the relevant gene may encode the toxin or a protein involved (or more preferably required) for the efficient production thereof, such that the attenuation reduces the level of toxin produced. Preferably one such gene is partially or fully deleted.

A preferred gene is the sagA gene, essential to production of the streptolysin S haemolytic toxin. Work in *Streptococcus pyogenes* has identified that injection site lesions could be reduced by inactivation of the SLS haemolytic toxin in this Group A Streptococci (Betschel et al., 1998).

Immunogenicity

The attenuation of genes leading to immune evasion will lead to increased immunogenicity.

Immune evasion in this context is used broadly to cover situations both in which an immune response is directly suppressed, and also where it is misdirected—for example by so-called "superantigens", which exhibit highly potent lymphocyte-transforming (mitogenic) activity directed towards T lymphocytes.

Example genes may encode enzymes or other proteins involved in production of the hyaluronate capsule.

Preferably one such gene is partially or fully deleted.

A preferred gene is the hasA gene which has been described in relation to *Streptococcus pyogenes* (Dougherty and van de Rijn 1994, Wessels et al., 1994).

Other preferred genes may encode superantigen toxins. Although these are toxins in their own right, it is believed that their primary effect may be to misdirect the immune response. Examples of such genes are seeH, seeI, seeL and seeM (Artiushin et al., 2002, Proft et al., 2003). Deletion or truncation of these genes therefore increases the immunogenicity of the vaccine.

Other preferred genes, slaA and slab encode putative phospholipase A2 toxins, which have homology with a gene recently identified in *S. pyogenes* (Beres et al., 2002). These are likewise believed to be virulence factors, which exert a profound effect on the proinflammatory cascade as well as having neurotoxic, myotoxic and anticoagulant properties.

Preferably 1, 2, 3, 4, 5, 6 or all 7 of these genes are attenuated.

Serological Discrimination

The modification of one or more genes which permit serological discrimination of the vaccine strain may be useful in differentiating vaccinated subjects from those exposed to virulent pathogens. This permits the evaluation of the contribution of the vaccination to disease prevention and in the management of outbreaks in vaccinated populations.

A preferred target gene is that which encodes the M protein.

Vaccines based on the full length M-protein have previously shown poor efficacy in horses despite excellent immunogenicity (Sheoran et al., 2002). Truncation such as to remove regions of the IgG and\or fibrinogen binding functional domains may further attenuate the vaccine strain (see also Meehan et al., 2000, Meehan et al., 2001). Lack of the fibrinogen and IgG binding domains may lower the risk of induction of the immune complex disease purpura haemorrhagica occasionally associated with strangles and strangles vaccines, including those based on the M-protein (Galan and Timoney 1985, Pusterla et al., 2003, Herwald et al., 2004).

Other preferred target genes encode the superantigen toxins seeH, seeI, seeL and seeM (Artiushin et al., 2002, Proft et al., 2003; see above).

Recombination Repair

Example genes may encode recombinases or other nucleic acid modifying enzymes responsible for repair or recombination. Preferably one such gene is partially or fully deleted such as to reduce the possibility of strain reversion i.e. when the above are combined with impairment of an enzyme responsible for recombination repair of the genome a live attenuated vaccine essentially incapable of repairing the attenuating deletions may be achieved.

A preferred gene is the recA gene (Tao et al., 1995). Deletion of recA may have the added advantage of increasing the sensitivity of the vaccine strain to UV light, decreasing the likelihood of environmental persistence.

Preferred Strains

Thus preferred strains may combine modifications (i) and (ii) with one or more of (iii), (iv) and (v), preferably two of (iii), (iv) and (v), most preferably all three of (iii), (iv) and (v).

Preferably the strain will be engineered such that no plasmid DNA or antibiotic resistance genes remain present, such as to maintain the same sensitivity to antibiotics as the parental strain.

Preferably the *Streptococcus* is a Beta-haemolytic *streptococcus*, for example in Lancefield group C—however as noted above *Streptococcus* pathogens share significant genetic identity and hence express near identical toxins and virulence factors.

In one embodiment the *Streptococcus* is *S. equi* which is causative of strangles. The present inventors have rationally selected and designed a combination of the above modifications to generate a novel live attenuated vaccine strain known as "SHMAPR" that can be more widely applied throughout the equine community. This combines the following properties:

To reduce injection site reactions and improve safety, the sagA gene was partially deleted. To improve the immunogenicity, the hasA gene was partially deleted. Consequently, the train appears non-haemolytic and non-mucoid on blood agar plates and so is readily distinguished from wild-type strains.

It should be noted that deletion of the aroA gene (see above) would enable the strain to be differentiated at a genetic level from virulent *S. equi* (Kelly et al., 2006). However, as this gene has a near identical homologue in *S. zooepidemicus*, it cannot be utilised to develop a differential diagnostic ELISA to rapidly determine if vaccinated animals have sero-converted on subsequent exposure to strangles. To enable serological discrimination between vaccinated and naturally infected horses the M-protein was C-terminally truncated. To attenuate the strain the genes aroB and pyrC were partially deleted although despite this partial deletion the vaccine strain grows well in rich media. Finally, to further reduce the possibility of strain reversion the recA gene was partially deleted.

The SHMAPR *S. equi* vaccine strain was attenuated when administered via the IN, IM and subcutaneous (SC) routes in a mouse infection model. IN challenge of 30 mice, with $4\times10^6$ colony forming units (cfu) of the SHMAPR strain did not cause any signs of disease (Example 3). IM challenge of 5 mice, with $4\times10^6$ colony forming units (cfu) of the SHMAPR strain did not cause any signs of disease distal to the injection site and injection site reactions did not exceed the mild severity limit (Example 4). SC vaccination of mice with $10^5$ or $10^6$ cfu of the SHMAPR vaccine strain was also well tolerated. All 5 mice gained weight during the course of the study (Example 5). The majority of IM and SC vaccinated mice developed small pustules at the injection site containing live SHMAPR bacteria, indicative of immune recognition. Such short-term persistence of bacteria is likely to be beneficial for induction of immunity and has previously been noted for TW 928 in horses. Recovered bacteria maintained the non-haemolytic and acapsular phenotypes, confirming the in vivo stability of these deletions. In contrast, mice receiving similar doses of the wild type 4047 strain via the IN or IM routes fell ill and were all euthanased on ethical grounds within 24 hours. In this model an IN 4047 challenge dose of $10^3$ cfu induced disease in 4/5 mice within one week. Therefore, the SHMAPR vaccine strain is non-toxic and $>5\times10^3$-fold attenuated when compared to the parental strain in mice by IN challenge.

The SHMAPR live attenuated vaccine was also found to be safe in six ponies by intranasal and intramuscular administration at doses of $1\times10^9$ cfu and up to $1\times10^9$ cfu, respectively (Example 6). This intranasal dose of virulent *S. equi* 4047 has previously been shown to induce disease in 96% of control ponies (Hamilton et al., 2006, Waller et al., 2007 and Waller unpublished data).

The intranasal vaccination phase proceeded without incident. No significant injection site reactions were observed in any of the six ponies intramuscularly vaccinated with the SHMAPR live attenuated vaccine.

Thus vaccines as described herein may combine stability, safety and immunogenicity such as to permit for the possibility of intramuscular vaccination with reduced risk of harmful side effects or strain reversion. It will be appreciated that given the similarities of strategies of various Streptococcal pathogens, corresponding changes in other strains may likewise be expected to provide the benefits disclosed herein. Thus in another embodiment, the invention provides SHMAPR-modified vaccines based on non-*S. equi* strains, for example those shown in Table 7.

In Tables 7a and 7b homologues of certain preferred target genes described herein are described.

Referring to the Tables, where sequencing of the relevant strains has not yet been performed ("not available") it will be appreciated that those skilled in the art can nevertheless practice the present invention (in the light of the present disclosure) by identifying the homologues by conventional methods—for example PCR, blotting or the like (see, for example, Molecular Cloning: a Laboratory Manual: 2nd edition, Sambrook et al, 1989). The identification of such genes does not per se form part of the invention.

Referring to the Tables, if a homolog of a gene is believed not to be present in the relevant strain ("none") then it will be appreciated that modification of that gene in that strain is not required by the present invention.

Other particular preferred strains include also those strains shown in Table 8.

In one aspect, the invention provides *S. equi* strain SHMAPR, as deposited at the National Collection of Type Cultures (NCTC), Health Protection Agency, Centre for Infections 61, Colindale Avenue, LONDON NW9 5EQ, United Kingdom under accession number: 13412.

Thus in all aspects and embodiments described herein (e.g. strains, methods, processes, vaccines) this is optionally a preferred strain.

The invention further relates to a microbiological pure culture comprising bacteria according to the deposited strain. It goes without saying that next generations of bacteria from the deposited strain are also included.

The culture can e.g. be obtained by growing said bacteria at a temperature between 30 and 41° C. Bacteria can be grown e.g. in Todd Hewitt medium.

Production of Vaccines

The invention further provides a process for producing a *Streptococcus* vaccine strain, which process comprises:

(a) making the following modifications to its genome:
  (i) attenuation of one or more essential biosynthetic genes,
  (ii) attenuation of one or more genes which encode a haemolytic toxin, or protein involved in the production thereof, plus preferably any one, two, or most preferably three of the following modifications:
  (iii) attenuation of one or more genes which encode a protein responsible for reduced immunogenicity,
  (iv) modification of one or more genes such as to permit serological discrimination of the vaccine strain based on analysis of a protein encoded by said genes, and
  (v) attenuation of one or more genes which encode an enzyme responsible for recombination repair of the genome.

(b) optionally culturing the resulting strain.

The choice of genes may include any of those described above. As noted above, well-defined and deliberately made mutations involving the deletion of fragments of the gene or even the whole gene or the insertion of heterologous DNA-fragments or both, have the advantage, in comparison to classically induced mutations, that they will not readily revert to the wild-type situation. Thus, in one embodiment, the attenuation is deletion of at least 100 nucleotides. In one embodiment the deletion corresponds to that shown in any of Sequence Annexes 1-6. Optionally the primers described in the Examples hereinafter may be used in the preparation of deletions. These primers and their use in the process of this aspect thus form another aspect of the invention.

The vaccine strain (optionally obtained from culturing as described above, or from the relevant depositary institution) may be used in a process to prepare a vaccine, whereby it is combined with a pharmaceutically acceptable carrier.

The vaccine may be freeze dried, as described in more detail below.

The invention further provides a vaccine for vaccination against a Streptococcal pathogen as described herein comprising live bacteria of any *Streptococcus* attenuated vaccine strain described above and a pharmaceutically acceptable carrier. Such a carrier may be as simple as water, but it may e.g. also comprise culture fluid in which the bacteria were cultured. Another suitable carrier is e.g. a solution of physiological salt concentration.

Methods and Uses of Vaccines

In all vaccines, methods and uses described herein the vaccine is preferably a live vaccine. However use of inactivated (killed) vaccine formulations is also embraced by the present invention, should that be preferred by the user.

The invention further provides a method for immunising a subject against a Streptococcal pathogen, which method comprises administering to said subject the respective *Streptococcus* attenuated vaccine strain described above in sufficient amount to raise a protective immune response thereto.

"Respective" in this context means either the Streptococcal pathogen which was attenuated to produce the vaccine strain, or a different pathogen which is sufficiently immunologically cross reactive such that the vaccine strain provides protection therefrom.

For example in one embodiment an *S. equi* vaccine strain may be used for combating *Streptococcus equi* or *Streptococcus zooepidemicus* infection in horses.

Preferably the method is for vaccination against a disease shown in Table 7, by use of the appropriate live vaccine strain prepared according to the present invention.

It will be appreciated by those skilled in the art that immunisation, or protection, in this context does not necessarily circumscribe complete success (i.e. that a subject so vaccinated would never be susceptible to infection by said pathogen). Rather it is used in its art-recognised sense to be a prophylactic measure with the aim of mitigating the severity of, or reducing the incidence of, said infection.

Strains described herein may be "avirulent" by which it would be understood not to be able to cause the relevant disease in the subject and includes those which a person of skill in the art would consider safe for administering to the subject as a vaccine. For example, in the context of a strangles vaccine, a strain causing minor clinical signs, including fever, serous or mucopurulent nasal discharge or ocular discharge, is within the scope of the present invention since such clinical signs are considered acceptable vaccine side effects.

In other aspects the invention provides:

Use of *Streptococcus* attenuated vaccine strain described above in sufficient amount to raise an immune response thereto in a method for immunising a subject against the respective *Streptococcus* pathogen;

A *Streptococcus* attenuated vaccine strain described above for use in a method for immunising a subject against the respective *Streptococcus* pathogen;

Use of *Streptococcus* attenuated vaccine strain described above in the preparation of a medicament for immunising a subject against the respective *Streptococcus* pathogen. The medicament may comprise a sufficient amount or dose to raise an immune response thereto in the subject.

Modes of Administration and Dosage

A vaccine according to the present invention can be administered in various forms. It can e.g. be administered parenterally, e.g. intramuscularly, subcutaneously or intradermally, it can also be given orally, submucosally (e.g. in the lip) or it can be given intranasally.

In respect of strangles, the nasal mucosa is the most common porte d'entree for *Streptococcus equi* infection. Therefore, the nose is the most natural place for the application of the live attenuated vaccine according to the invention. In addition, this application site has the advantage that it is easily reached, and that the vaccine can e.g. be administered by spraying. Thus, in one preferred form, the vaccine of the present invention is suitable for intranasal application. Other vaccines are commonly administered via the intramuscular route. The SHMAPR live attenuated vaccine has been specifically designed such that this route can be utilised. Therefore, in another preferred form, the vaccine of the present invention is suitable for intramuscular application. Due to its attenuated characteristics, the vaccine can be used to protect horses at any age, including young horses e.g. between 6 and 12 months of age.

A vaccine according to the present invention may comprise any dose of bacteria, sufficient to evoke an immune response. Doses ranging between $10^3$ and $10^9$ bacteria are e.g. very suitable doses.

A vaccine according to the present invention may comprise any volume of bacteria, suitable for the route of administration selected. Volumes ranging between 0.2 ml and 2 ml bacteria are e.g. very suitable for intramuscular administration. Volumes ranging between 2 ml and 20 ml bacteria are e.g. very suitable for intranasal administration.

A vaccine according to the present invention may be administered using a variety of different dosing regimens, sufficient to evoke an immune response. Doses administered between 2 and 12 weeks are e.g. very suitable for naïve animals. Doses administered between 12 and 52 weeks are e.g. very suitable for primed animals.

Storage

There are several ways to store live organisms. Storage in a refrigerator is e.g. a well-known method. Also often used is storage at −70° C. in a buffer containing glycerol. Bacteria can also be kept in liquid nitrogen. Freeze-drying is another way of conservation. Freeze-dried bacteria can be stored and kept viable for many years. Storage temperatures for freeze-dried bacteria may well be above zero degrees, without being detrimental to the viability. Freeze-drying can be done according to all well-known standard freeze-drying procedures.

Optional beneficial additives, such as e.g. skimmed milk, trehalose, gelatin or bovine serum albumin can be added in the freeze-drying process. Therefore, in a more preferred form, the vaccine is in a freeze-dried form.

Other Vaccine Constituents

In another embodiment, the vaccine of the present invention additionally comprises another attenuated pathogen or antigenic material from another pathogen. Such a pathogen may e.g. be another bacterium or a parasite. Also it can be of viral origin. Usually, the other pathogen or antigenic material thereof will be a horse pathogen. A vaccine according to the invention that also comprises such an additional attenuated pathogen or antigenic material from another pathogen has the advantage that it induces protection against several infections at the same time. Horse pathogens or antigenic material thereof that can advantageously be added are e.g. Potomac fever agent, *Rhodococcus equi, Clostridium botulinum Clostridium tetanii, Burkholdiera mallei, Streptococcus zooepidemicus*, Vesicular Stomatitis Virus, Borna disease virus, Equine influenza virus, African horse sickness virus, Equine arteritis virus, Equine herpesvirus 1-4, Infectious anemia virus, Equine encephalomyelitis viruses (Eastern, Western and Venezuelan), West Nile virus, Rabies virus, Hendra disease virus and Japanese B encephalomyelitis virus.

The vaccine may also comprise an adjuvant. Adjuvants are non-specific stimulators of the immune system. They enhance the immune response of the host to the invading pathogen. Examples of adjuvants known in the art are Freunds Complete and Incomplete adjuvant, vitamin E, non-ionic block polymers, muramyldipeptides, ISCOMs (immune stimulating complexes, cf. for instance EP 109942), Quill A, mineral oil, vegetable oil, and Carbopol (a homopolymer).

Adjuvants, specially suitable for mucosal application are e.g. the *E. coli* heat-labile toxin (LT) or Cholera toxin (CT).

In addition, the vaccine may comprise one or more stabilisers. Also, the vaccine may comprise one or more suitable emulsifiers, e.g. Span or Tween.

Thus in all aspects and embodiments described herein (e.g. strains, methods, processes, vaccines) the following may optionally be included along with the vaccine strain:

a) Stabilising proteins to facilitate freeze-drying e.g. any described above.

b) Adjuvant e.g. selected from the group consisting of *E. coli* heat-labile toxin and Cholera toxin.

c) Other attenuated pathogen or antigenic material from another pathogen, as appropriate to the subject to be treated (i.e. to product a multivalent vaccine). For example, a multivalent vaccine suitable for use in horses may include attenuated pathogen or antigenic material therefrom, from the group consisting of Potomac fever agent, *Rhodococcus equi, Clostridium botulinum Clostridium tetanii, Burkholdiera mallei, Streptococcus zooepidemicus*, Vesicular Stomatitis Virus, Borna disease virus, Equine influenza virus, African horse sickness virus, Equine arteritis virus, Equine herpesvirus 1-4, Infectious anemia virus, Equine encephalomyelitis viruses (Eastern, Western and Venezuelan), West Nile virus, Rabies virus, Hendra disease virus and Japanese B encephalomyelitis virus.

The resulting strains, methods, processes, vaccines etc. including one or more of these things form other aspects of the invention.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1: Relative location of the primers described in the Examples below.

Figure 2:
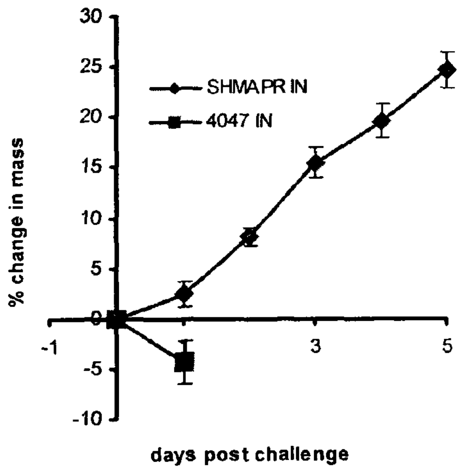

FIG. 2: Mean % change in mass following intranasal challenge with *S. equi* 4047 or SHMAPR. Error bars indicate 95% confidence intervals.

Figure 3:
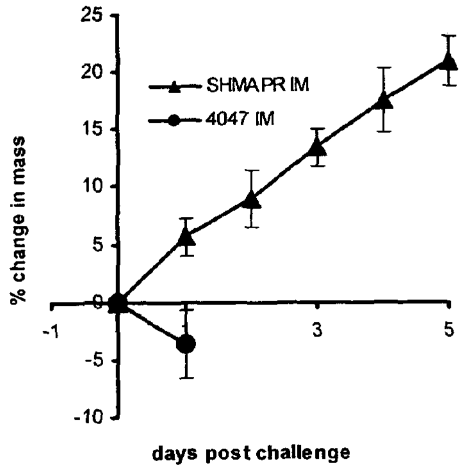

FIG. 3: Mean % change in mass following intramuscular challenge with *S. equi* 4047 or SHMAPR. Error bars indicate 95% confidence intervals.

Figure 4:
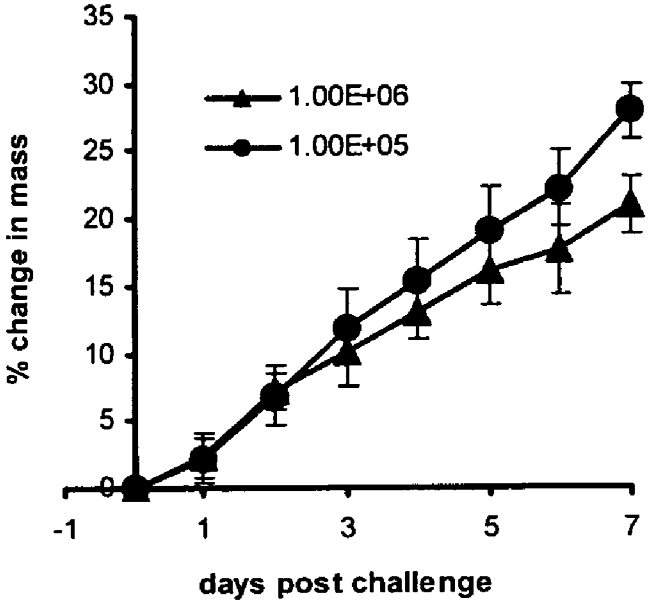

FIG. 4: Mean % change in mass following subcutaneous challenge with $1\times10^6$ or $1\times10^5$ cfu of *S. equi* SHMAPR. Error bars indicate 95% confidence intervals.

Figure 5:
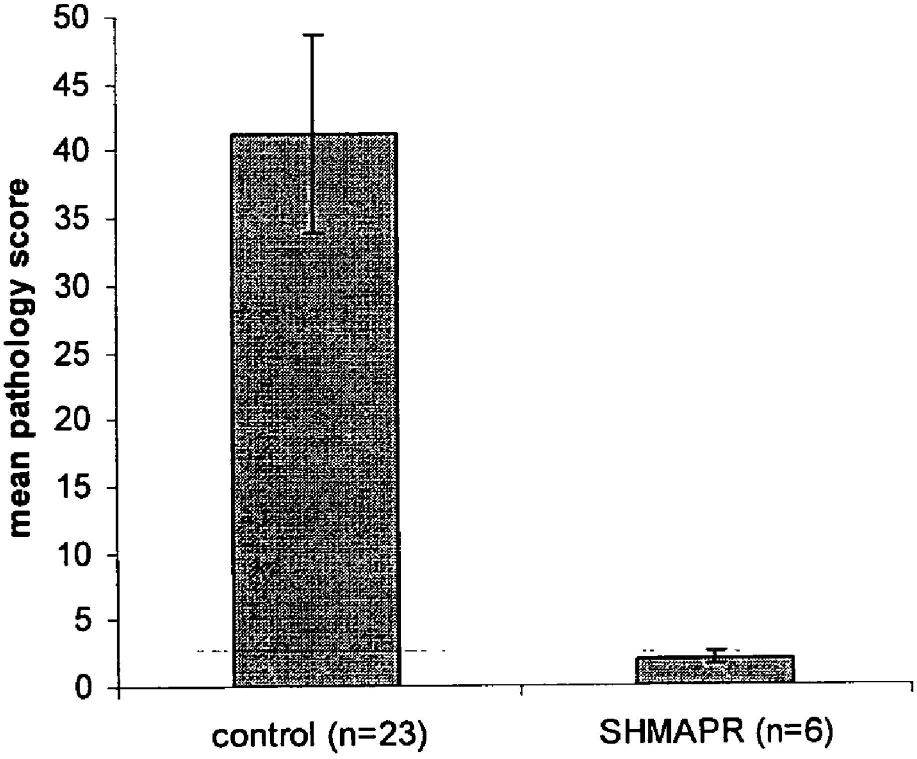

FIG. 5: Mean pathology score in control and SHMAPR challenged ponies. Control data represents the mean of 4 independent challenges with *S. equi* 4047 in a total of 23 ponies (Hamilton et al., 2006, Waller et al., 2007 and Robinson, unpublished data). Error bars represent the 95% confidence interval.

Figure 6:
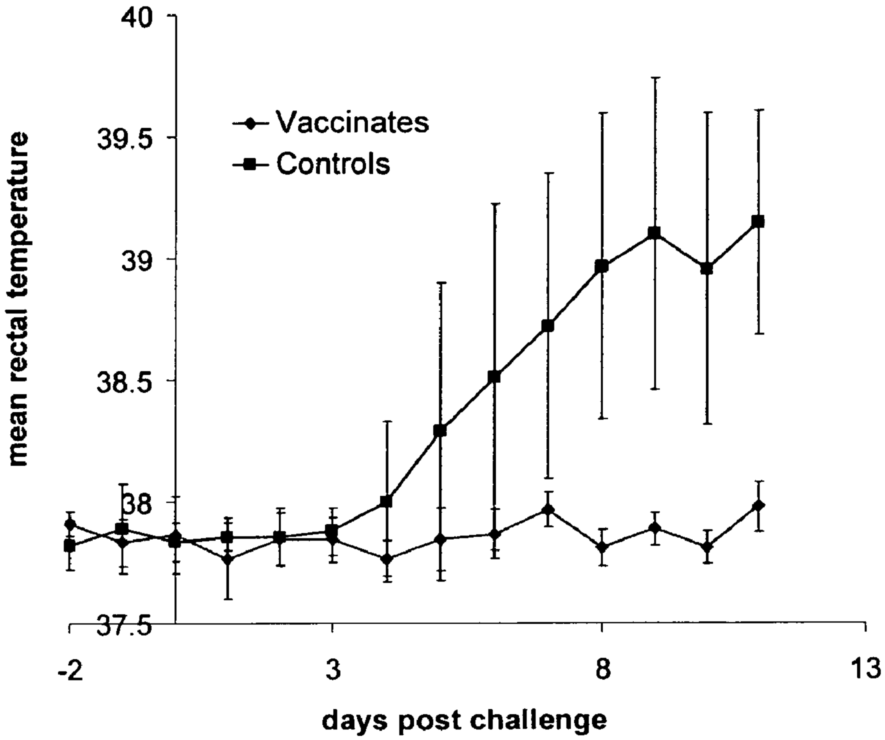

FIG. 6: Mean rectal temperature. Error bars indicate 95% confidence interval.

Figure 7:
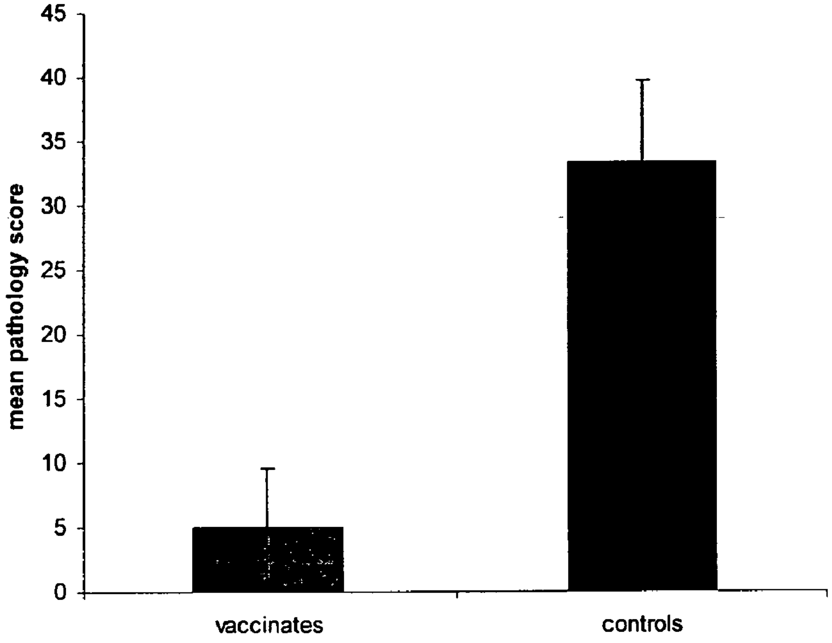

FIG. 7: Mean pathology score. Error bars indicate 95% confidence interval.

SEQUENCE ANNEXES 1-6

Sequence Annex 1—sagA deletion:
Sequence Annex 2—hasA deletion:
Sequence Annex 3—seM deletion:
Sequence Annex 4—aroA deletion:
Sequence Annex 5—pyrC deletion:
Sequence Annex 6—recA deletion:

EXAMPLES

Example 1

Selection of a Mutant Strain

An example vaccine was derived from a field isolate of *Streptococcus equi* responsible for causing strangles in a New Forest pony in Hampshire in 1990 and is the subject of the *Streptococcus equi* genome-sequencing project. The field strain was designated strain 4047. This strain was grown overnight, aerobically at 37° C., on blood agar and then inoculated in Todd Hewitt medium and subjected to well-described DNA mutation techniques (Maguin et al., 1992) to achieve the desired vaccine characteristics.

Briefly, the partial deletion of each target gene was performed as follows:

Upstream and downstream pieces of DNA homologous to the target gene were cloned into the pGhost9 plasmid via EcoRI and SalI restriction sites to create a copy of the target gene lacking the desired internal portion of the coding sequence. Details of the primers used to generate the required plasmids, the section of the genes to be deleted and a schematic for primer use can be found in Tables 1 and 2 and FIG. 1.

pGhost9 plasmid containing the desired homologous DNA was then transformed into competent *Streptococcus equi* strain 4047 via electroporation and strains containing the plasmids were grown for 48 hours at 28° C. on Todd Hewitt medium with 0.5 μg of erythromycin per ml. An overnight (16 h) culture was diluted 100-fold in Todd Hewitt medium containing erythromycin and incubated at 28° C. until on $OD_{600}$ of 0.3 was reached (mid exponential phase). The culture was then shifted to 37.5° C. for 150 min to initiate integration of the plasmid in to the chromosome by homologous recombination, as the plasmid can not replicate at 37° C.

Samples were diluted and plated at 37° C. on Todd Hewitt agar containing 0.5 μg of erythromycin per ml (to identify insertion mutants) and without erythromycin (to determine the viable cell count). Integration of the plasmid into the chromosome was confirmed by PCR.

To excise the inserted vector and generate the desired gene deletion, insertion mutants were grown overnight in Todd Hewitt medium (without erythromycin) at 37° C. The culture was then diluted $10^3$-fold in Todd Hewitt medium and incubated at 28° C. without erythromycin, until stationary phase (about 18 h); this step stimulates recombination by allowing plasmid replication. Cultures were then diluted and plated without erythromycin at 37° C., to allow loss of the excised plasmid. Colonies were transferred with toothpicks to selective (containing 0.5 μg of erythromycin per ml) and non-selective plates. Colonies in which excision had occurred were phenotypically erythromycin sensitive.

Deletion mutant strains were identified by PCR across the desired deletion site. In such experiments a smaller target gene DNA fragment was amplified from the desired deletion mutant strain when compared with the parental *Streptococcus equi* 4047 strain (Table 2).

Each gene was deleted sequentially in the order sagA, hasA, seM, aroB, pyrC and recA. recA was deleted last as the deletion process requires the presence of the recA gene product.

A strain with deletions in the genes sagA, hasA, seM, aroB, pyrC and recA was selected and designated SHMAPR. PCR was performed across each of the deleted target genes using the primers in Table 1 and the products purified and sequenced on an ABI3100 automated sequencer using well-described protocols to confirm that the desired deletions had been generated. Details of each deletion generated are presented in Table 2.

Owing to deletion of part of the sagA gene, the SHMAPR strain appears non-haemolytic on blood agar plates.

Owing to deletion of part of the hasA gene, the SHMAPR strain appears non-mucoid on agar plates and sediments in liquid culture.

TABLE 1

| Target gene | Primer name | Primer sequence | |
|---|---|---|---|
| sagA | 5'sagA[1] | GGG**GAATTC**TGAGGTACTAGCCATCTGTC | (SEQ ID NO: 13) |
| | sagA NDEL[2] | GGG**AAGCTT**AGCAAATTGTAACATAATGCTTACC | (SEQ ID NO: 14) |
| | sagA CDEL[3] | GGG**AAGCTT**GCTGAGCCAAAAGCGTAAAC | (SEQ ID NO: 15) |
| | 3'sagA[4] | GGG**GTCGAC**AAAACTCAGCCACACTGGTC | (SEQ ID NO: 16) |
| hasA | 5'hasA2[1] | GGG**GAATTC**AAGGGAAGGGCTGGGCAATATAAGG | (SEQ ID NO: 17) |
| | hasA NDEL[2] | GGG**GATATC**ATTTCTGACATTAAGGTGACCCGTC | (SEQ ID NO: 18) |
| | hasA CDEL[3] | GGG**GATATC**TGGAACAAGTCCTTCTTTAGAGAG | (SEQ ID NO: 19) |
| | 3'hasA2[4] | GGG**GTCGAC**AGGGCTGTAGGACAAACAAATGCAG | (SEQ ID NO: 20) |
| seM | 5'SEM stop[1] | GGG**GAATTC**ATGTTTTAGAGAAATAACAAGC | (SEQ ID NO: 21) |
| | SEM NDEL stop[2] | GGG**GATATC**ATTTTACATCGATGAAAGGTG | (SEQ ID NO: 22) |
| | SEM CDEL stop[3] | GGG**GATATC**TGAGATGCTAAGGTAGCAGAGC | (SEQ ID NO: 23) |
| | 3'SEM CENT[4] | GGG**GTCGAC**GTTTTCTTTGCGTTTAGGAGACACC | (SEQ ID NO: 24) |
| aroB | ASW31[1] | GAC**GAATTC**TGTCTGAAAGGCAGCTAGAG | (SEQ ID NO: 25) |
| | ASW32[2] | GAC**GACGAT**ATCGGATAGTCATTGATACGAGAC | (SEQ ID NO: 26) |
| | ASW33[3] | GCTA**GATATC**GCCTGAGAAGGCT | (SEQ ID NO: 27) |
| | ASW34[4] | GACGAC**GTCGAC**TGGTAAGACCTGGACAACAG | (SEQ ID NO: 28) |
| | ZM24[5] | ACACCTGATCTTGCCTTGTC | (SEQ ID NO: 29) |

TABLE 1-continued

| Target gene | Primer name | Primer sequence | |
|---|---|---|---|
| pyrC | ASW35[1] | GAC**GAATTC**GCAGCAGATATTGGAGTAAGG | (SEQ ID NO: 30) |
| | ASW36[2] | GACGAC**AAGCTT**GCCACCTGATCTAGCTGTGAT | (SEQ ID NO: 31) |
| | ASW37[3] | GACGAC**AAGCTT**AGCGTTTGGTAACAGAAGCC | (SEQ ID NO: 32) |
| | ASW38[4] | GACGAC**GTCGAC**TACGTTTCGGATTCTTGGGC | (SEQ ID NO: 33) |
| | ZM23[5] | GGCAGGCTATTATGGCTAAG | (SEQ ID NO: 34) |
| recA | ASW57[1] | GACGAC**GAATTC**TTATTGCTTGCTAGTCAGCC | (SEQ ID NO: 35) |
| | ASW58[2] | GACGAC**GATATC**AAGGCTGCAATACCACCTTC | (SEQ ID NO: 36) |
| | ASW59[3] | GACGAC**GATATC**GAAGGCATCTCACGTACAGG | (SEQ ID NO: 37) |
| | ASW60[4] | GACGAC**GTCGAC**TTGACGATCGCTGTTAAGCC | (SEQ ID NO: 38) |

[5]Additional primer used for sequencing.
Restriction sites used for cloning are in bold.

TABLE 2

| Target gene | Size of deleted PCR product | Size of 4047 strain PCR product | Gene size | Deletion generated | Deletion size |
|---|---|---|---|---|---|
| sagA | 945 bp | 1071 bp | 165 bp | 16 bp to 141 bp | 126 bp |
| hasA | 722 bp | 1033 bp | 1254 bp | 577 bp to 888 bp | 311 bp |
| seM | 810 bp | 1620 bp | 1605 bp | 349 bp to 1158 bp | 810 bp |
| aroB | 1243 bp | 2270 bp | 1083 bp | 46 bp to 1073 bp | 1027 bp |
| pyrC | 1387 bp | 2472 bp | 1413 bp | 204 bp to 1288 bp | 1085 bp |
| recA | 731 bp | 1257 bp | 1152 bp | 330 bp to 855 bp | 526 bp |

The SHMAPR vaccine strain was then tested for its attenuated character as described in the Examples below.

Example 2

Preparation of Vaccine

*Streptococcus equi* strain SHMAPR and the wild type parent 4047 strain were grown overnight, aerobically at 37 degree. C., on blood agar and then inoculated in Todd Hewitt medium containing 10% foetal calf serum. For the vaccination/challenge studies, the strains were cultured for 6 hours at 37 degree. C. in 100 ml of Todd Hewitt medium containing 10% foetal calf serum to an $OD_{600nm}$ of 0.3. At this density the viable number of *S. equi* is $2\times10^8$ cfu/ml.

Example 3

Intranasal Safety Test of the Vaccine Strain SHMAPR in Mice

In this example, the rate of attenuation of the *S. equi* SHMAPR as compared to the wild-type strain 4047 has been tested in mice. $4\times10^8$ CFU of the mutant strain as well as the parent 4047 wild-type strain were applied intranasally to mice and mortality was recorded.

Animals

BALB/c mice, 4 weeks of age, obtained from Charles River Ltd, were used for the experiment.

Vaccination/Challenge Cultures

*Streptococcus equi* strain SHMAPR and the wild type parent 4047 strain were grown overnight, aerobically at 37° C., on blood agar and then inoculated in Todd Hewitt medium containing 10% foetal calf serum. The strains were then cultured for 6 hours at 37° C. in 20 ml of Todd Hewitt medium containing 10% foetal calf serum to an $OD_{600nm}$ of 0.3. At this density the viable number of *S. equi* is $2\times10^8$ cfu/ml.

Treatment

At 4 weeks of age, 1 group of 30 mice sedated with 100 mg/kg ketaset, was challenged intranasally (20 μl) with $4\times10^6$ cfu *S. equi* strain 4047 and 1 group of 30 mice sedated with 100 mg/kg ketaset, was treated intranasally with $4\times10^6$ cfu *S. equi* strain SHMAPR.

After the treatments, clinical signs of disease, weight loss and mortality was recorded for 5 days. Histopathological examination of all mice was used to determine the extent of disease progression.

Results:

The results after intranasal challenge of 4 weeks old mice with $4\times10^8$ cfu strain 4047 or strain SHMAPR are shown in Table 3.

A severe infection in 28/30 mice challenged with the 4047 strain was observed within 24 hours. All mice in the wild type challenge groups were humanely euthanased at or before 24 hours after initial challenge. On post mortem examination, it was apparent that these mice had died from pneumonia and septicaemia rather than the more classical clinical course of strangles.

None of the 30 mice challenged with an identical dose of *S. equi* SHMAPR showed any clinical signs of disease. All mice continued to gain weight (FIG. 2). Histopathological examination of all mice 5 days post infection identified only mild signs of infection in 6/30 mice.

TABLE 3

| Group | Number of mice | Route | Dose | Mortality | Clinical signs of disease | Histopathological disease |
|---|---|---|---|---|---|---|
| 4047 | 30 | IN | $4\times10^6$ | 30 (on day 1) | 28 | 29 |
| SHMAPR | 30 | IN | $4\times10^6$ | 0 (by day 5) | 0 | 6 |

Conclusions

Other experiments following the same methods for strain preparation and administration have determined that an intranasal dose of $1\times10^3$ cfu of *S. equi* 4047 was sufficient to induce clinical disease in 4 of 5 mice at 5 days post challenge (Waller, unpublished data). Therefore, the SHMAPR strain is over $5\times10^3$-fold attenuated in the intranasal mouse challenge model. The mild histological signs identified in 6/30 SHMAPR challenged mice indicates that this strain can stimulate an immune response in mice.

Example 4

Intramuscular Safety Test of the Vaccine Strain SHMAPR in Mice

In this example, the rate of attenuation of the *S. equi* SHMAPR as compared to the wild-type strain 4047 has been tested in mice. $4\times10^6$ CFU of the mutant strain as well as the parent 4047 wild-type strain were applied intramuscularly into the left leg of mice and mortality was recorded.

Animals

BALB/c mice, 4 weeks of age, obtained from Charles River Ltd, were used for the experiment.

Vaccination/Challenge Cultures

*Streptococcus equi* strain SHMAPR and the wild type parent 4047 strain were grown overnight, aerobically at 37° C., on blood agar and then inoculated in Todd Hewitt medium containing 10% foetal calf serum. The strains were then cultured for 6 hours at 37° C. in 20 ml of Todd Hewitt medium containing 10% foetal calf serum to an $OD_{600nm}$ of 0.3. At this density the viable number of *S. equi* is $2\times10^8$ cfu/ml.

Treatment

At 4 weeks of age, 1 group of 5 mice was challenged intramuscularly (20 µl) with $4\times10^8$ cfu *S. equi* strain 4047 and 1 group of 5 mice was challenged intramuscularly (20 NI) with $4\times10^8$ cfu *S. equi* strain SHMAPR.

After the treatments, clinical signs of disease, weight loss and mortality was recorded for 5 days. Histopathological examination of all mice was used to determine the extent of disease progression.

Results:

The results after intramuscular challenge of 4 weeks old mice with $4\times10^8$ cfu strain 4047 or strain SHMAPR are shown in Table 4.

On day 1, all 5 mice injected IM with *S. equi* 4047 had severe swelling of their left leg and had ruffled coats. All of these mice looked very ill and were euthanased. All 5 mice injected with the SHMAPR strain developed swollen left legs, but remained active throughout the study. By day 5 one mouse had resolved its mild injection site reaction. All *S. equi* SHMAPR challenged mice gained weight as normal during the study period (FIG. 3).

On post mortem examination, 1 mouse challenged with *S. equi* 4047 had developed histological disease away from the injection site. None of the 5 mice challenged with an identical dose of *S. equi* SHMAPR had histological signs distal to the injection site. 4 SHMAPR vaccinated mice had small injection site pustules 5 days post challenge, from which the original *S. equi* SHMAPR strain was isolated, highlighting that the SHMAPR strain can persist for a short time at the injection site.

TABLE 4

| Group | Route | Dose | Number of mice | Mortality | Clinical signs of disease | Histopathological disease |
|---|---|---|---|---|---|---|
| 4047 | IM | $4\times10^6$ | 5 | 5 (on day 1) | 5 | 1 |
| SHMAPR | IM | $4\times10^6$ | 5 | 0 (by day 5) | 0 | 0 |

Conclusions

The *S. equi* SHMAPR strain produced dramatically less disease and injection site swelling than *S. equi* 4047 when injected intramuscularly. The SHMAPR strain could persist at the injection site for a short period of time, which may enhance the stimulation of the immune system. Injection site reactions in mice did not cause any clinical signs of disease and mice continued to gain weight normally during the study period. Therefore, the SHMAPR live attenuated vaccine appears ideally suited for intramuscular administration.

Example 5

Subcutaneous Safety Test of the Vaccine Strain SHMAPR in Mice

In this example, the safety of two doses of the *S. equi* SHMAPR was tested in mice. $1\times10^6$ or $1\times10^5$ CFU of the mutant strain were applied subcutaneously into the neck scruff of mice and mortality was recorded. No mice were challenged subcutaneously with parental strain 4047 because of the severe disease observed in earlier intranasal and intramuscular challenges with this strain.

Animals

BALB/c mice, 4 weeks of age, obtained from Charles River Ltd, were used for the experiment.

Vaccination/Challenge Cultures

*Streptococcus equi* strain SHMAPR was grown overnight, aerobically at 37° C., on blood agar and then inoculated in Todd Hewitt medium containing 10% foetal calf serum. The strain was then cultured for 6 hours at 37° C. in 20 ml of Todd Hewitt medium containing 10% foetal calf serum to an $OD_{600nm}$ of 0.3. At this density the viable number of *S. equi* is $2\times10^8$ cfu/ml.

Treatment

At 4 weeks of age, 1 group of 5 mice was challenged subcutaneously (10 µl) with $1\times10^6$ cfu *S. equi* strain SHMAPR and 1 group of 5 mice was challenged subcutaneously (10 µl) with $1\times10^5$ cfu *S. equi* strain SHMAPR.

After the treatments, clinical signs of disease, weight loss and mortality was recorded for 5 days. Histopathological examination of all mice was used to determine the extent of disease progression.

Results:

The results after subcutaneously challenge of 4 weeks old mice with $1\times10^6$ cfu or $1\times10^5$ cfu of strain SHMAPR are shown in Table 5.

All mice showed signs of injection site reactions, which did not exceed the mild severity limit. The injection site reaction in one mouse challenged with $1\times10^5$ cfu of SHMAPR resolved by day 7 post-challenge. All mice remained active and gained weight normally during the study period (FIG. 4).

On post mortem examination, none of the mice had histological signs distal to the injection site. 5/5 mice challenged subcutaneously with $1\times10^6$ cfu and 4/5 mice challenged subcutaneously with $1\times10^5$ cfu *S. equi* SHMAPR had small injection site pustules 7 days post challenge, from which the original *S. equi* SHMAPR strain was isolated, highlighting that the SHMAPR strain can persist for a short time at the injection site.

TABLE 5

| Group | Route | Dose | Number of mice | Mortality | Clinical signs of disease | Histopathological disease |
|---|---|---|---|---|---|---|
| SHMAPR | SC | $1\times10^6$ | 5 | 0 | 0 | 0 |
| SHMAPR | SC | $1\times10^5$ | 5 | 0 | 0 | 0 |

Conclusions

The *S. equi* SHMAPR strain was well tolerated by the subcutaneous route. All mice remained active and healthy throughout the study period. The SHMAPR strain could persist at the injection site for a short period of time, which may enhance the stimulation of the immune system. Injection site reactions in mice did not cause any clinical signs of disease and mice continued to gain weight normally during the study period. Differences in the % change in mass between the groups only became significant on day 7 and could be due to mouse/mouse variation given the small group sizes used. Therefore, the SHMAPR live attenuated vaccine also appears ideally suited for subcutaneous administration.

Example 6

Intranasal and Intramuscular Safety Test of the Vaccine Strain SHMAPR in Welsh Mountain Ponies In this example, the safety and immunogenicity of the SHMAPR vaccine strain in horses by intranasal and intramuscular vaccination was determined.

Animals

Six male Welsh Mountain Ponies supplied by Mr. R. Beedles, Shropshire, UK were used. Ponies were approximately 8 months of age at the time of the first vaccination.

Vaccination Cultures

*Streptococcus equi* strain SHMAPR and the wild type parent 4047 strain were grown overnight, aerobically at 37° C., on blood agar and then inoculated in Todd Hewitt medium containing 10% foetal calf serum. The strains were then cultured for 6 hours at 37° C. in 20 ml of Todd Hewitt medium containing 10% foetal calf serum to an $OD_{600nm}$ of 0.3. At this density the viable number of *S. equi* is approximately $2\times10^8$ cfu/ml.

Treatment

On day 0 the ponies received an intranasal dose of $1\times10^8$ cfu SHMAPR. This intranasal dose of virulent *S. equi* 4047 has previously been shown to induce disease in 96% of control ponies (Hamilton et al., 2006; Waller et al., 2007; Waller unpublished data).

On day 14 the ponies received an intramuscular dose of $1\times10^9$ cfu, $1\times10^8$ cfu or $1\times10^7$ cfu SHMAPR into the right side of their neck according to Table 6:

TABLE 6

| Group | Number of ponies/ID numbers | Intranasal vaccine dose | Intramuscular vaccine dose |
|---|---|---|---|
| A | 2/4277, 4530 | $1\times10^8$ cfu | $1\times10^9$ cfu |
| B | 2/5066, 5251 | $1\times10^8$ cfu | $1\times10^8$ cfu |
| C | 2/5756, 5793 | $1\times10^8$ cfu | $1\times10^7$ cfu |

Results:

The SHMAPR live attenuated vaccine was also found to be safe in six ponies by intranasal and intramuscular administration at doses of $1\times10^8$ cfu and up to $1\times10^9$ cfu, respectively.

The intranasal vaccination phase proceeded without incident. No increase in the size of submandibular lymph nodes or signs of mucopurulent nasal discharge were observed during this two week period.

Ponies were then intramuscularly vaccinated with $1\times10^9$ cfu, $1\times10^8$ cfu or $1\times10^7$ cfu of the SHMAPR live attenuated vaccine. No significant injection site reactions were observed in any of the vaccinated ponies and all ponies had normal neck movements and appetites, indicating that the SHMAPR vaccine can be safely administered via this vaccination route.

Following post mortem examination a small pustule containing the SHMAPR live attenuated vaccine strain was found in one pony vaccinated with $1\times10^8$ cfu of the SHMAPR live attenuated vaccine. The pustule did not appear to be progressing beyond the injection site. This type of lesion may be highly advantageous in stimulating a prolonged protective immune response against infection with a field strain. There was no evidence for spread of the SHMAPR strain to draining lymph nodes. These data demonstrate that the SHMAPR strain resulted in a much reduced intramuscular injection site lesion compared with published data using the Intervet live attenuated strain administered by the intramuscular route (Jacobs et al., 2000).

Conclusions

The SHMAPR live vaccine strain is safe in ponies for administration by the intranasal and intramuscular routes.

Example 7

Efficacy of the Vaccine Strain SHMAPR in Welsh Mountain Ponies

In this example, the efficacy of the SHMAPR vaccine strain in horses by intramuscular vaccination was determined after challenge with virulent *S. equi.*

Animals

Eighteen Welsh Mountain Ponies were used. Ponies were approximately 14 months of age at the time of the first vaccination.

Vaccination Cultures

*Streptococcus equi* strain SHMAPR and the wild type parent 4047 strain were grown overnight, aerobically at 37 degree C., on blood agar and then inoculated in Todd Hewitt medium containing 10% foetal calf serum. The strains were then cultured for 6 hours at 37 degree C. in 20 ml of Todd Hewitt medium containing 10% foetal calf serum to an $OD_{600nm}$ of 0.3. At this density the viable number of *S. equi* is approximately $2\times10^8$ cfu/ml. For vaccination, the required dose of SHMAPR was centrifuged for 10 minutes at 3000 rpm and resuspended in the appropriate volume of pre-warmed and gassed Todd Hewitt medium containing 10% foetal calf serum.

Treatment

On day 0 9 ponies received an intramuscular dose of $1\times10^8$ cfu SHMAPR in 200 μl Todd Hewitt medium containing 10% foetal calf serum. This dose of SHMAPR was previously shown to be safe over a two-week follow-up period via the intramuscular route (see example 6). The remaining 9 ponies were vaccinated with an equivalent volume of Todd Hewitt medium containing 10% foetal calf serum.

Ponies were monitored for 8 weeks and then a second vaccination was administered as above.

Ponies were monitored for a further 8 weeks and then challenged via administration of a dose of $1\times10^8$ cfu of virulent *S. equi* strain 4047. This dose has previously been shown to induce disease in >96% of horses.

Ponies were followed for signs of disease over a three week period. All ponies were then euthanased and subjected to post mortem examination. The number of abscesses formed in the lymph nodes of ponies were noted and the amount of disease in the vaccinated vs. control populations calculated.

Results:

Following the first vaccination, the SHMAPR live attenuated vaccine was found to slowly induce local injection site reactions in 4 of 9 ponies vaccinated. Earliest indications occurred two to three weeks post vaccination. Lesions were generally painless and did not result in loss of appetite, but were unsightly. Drainage of lesions was performed by a veterinary surgeon following sedation of affected ponies. The lesions in all four ponies then rapidly resolved. However, lesions in two of these ponies had not fully resolved at the time of the administration of the second vaccination and these ponies were not revaccinated. Both ponies had fully recovered shortly afterwards and were included in the challenge phase of the study.

Following the administration of the second vaccination to the remaining 7 ponies, slow forming injection site lesions occurred in one pony. This pony had been unaffected following the first vaccination. This lesion was drained; the pony made a full recovery and was included in the challenge phase of this study.

Following challenge with virulent *S. equi* 8 of 9 control ponies developed pyrexia over the 3 week observation period (mean number of days pyrexic=4.0). In contrast only one vaccinated pony developed pyrexia over the same period (mean number of days pyrexic=0.1) (FIG. 6). Ponies were euthanased as it became obvious that they had developed disease and before the rupture of lymph node abscesses on ethical grounds. The first control pony was euthanased 11 days post challenge and only 2 control ponies reached the endpoint of the study 18 days post challenge. All 9 vaccinated ponies reached the end of the study.

On post mortem examination abscesses were found in the retropharyngeal lymph nodes of all control ponies but only 2 of the 9 vaccinated ponies. One of these 2 vaccinated ponies had only received one vaccination. The mean pathology score for controls was 33.3 (±6.3) compared with a mean of 5.0 (±4.6) for vaccinated ponies (FIG. 7).

Conclusions

The SHMAPR live vaccine strain is efficacious for the prevention of strangles.

TABLE 7A most preferred genes and homologues

| Bacterium | Disease in animals | Disease in humans | sagA | hasA |
|---|---|---|---|---|
| *S. equi* (beta-haemolytic) | Strangles in horses. | | 0 | 0 |
| *S. zooepidemicus* (beta-haemolytic) Sequence at http://www.sanger.ac.uk/cgi-bin/blast/submitblast/s_zooepidemicus incomplete last accessed on Jul. 01, 2008 | Abortion, mastitis, keratitis, wound infections, abscesses in a wide variety of animals. | Nephritis, meningitis | Currently on contig zoo32c02.p1k Residues 203925-204086 | Currently on contig GZOO 1414 1396-1a02.w2k1396 residues 4614-5864 |
| *S. pyogenes* (beta-haemolytic) Sequence at http://www.sanger.ac.uk/Projects/S_pyogenes/ | None. | Necrotising facitis, pharyngitis, sepsis. | Residues 171838-172932 | Residues 1821324-1822563 |
| *S. uberis* http://www.sanger.ac.uk/Projects/S_uberis/ | Mastitis in cattle. | | NONE | Residues 1676849-1678089 |
| *S. pneumoniae* http://www.sanger.ac.uk/Projects/S_pneumoniae/23F/ | Pneumonia in horses. | Pneumonia | NONE | NONE |
| *S. agalactieae* NC_007432 | Mastitis in cattle | Neonatal meningitis, toxic shock, skin and soft tissue infections, bacteraemia | NONE | NONE |
| *S. suis* http://www.sanger.ac.uk/Projects/S_suis/ | Meningitis, septicemia, arthritis, bronchopneumonia, endocarditis, encephalitis, abortions and abscesses in pigs. | Meningitis, endocarditis spondylodiscitis, Streptococcal toxic shock syndrome, sepsis, arthritis, endophtalmitis, pneumonia | NONE | NONE |
| *S. iniae* (beta-haemolytic) http://www.hgsc.bcm.tmc.edu/bcm/blast/microbialblast.cgi Last searched on Jul. 25, 2007 | Meningiitis, panophthalmitis in fish Subcutaneous abscess in dolphins | Bacteraemic cellulitis | Contig 00719 residues 19433-19795 | Contig 00200 Residues 24289-25257 |

| Bacterium | SeM | aroB | pyrC | recA |
|---|---|---|---|---|
| *S. equi* (beta-haemolytic) | 0 | 0 | 0 | 0 |
| *S. zooepidemicus* (beta-haemolytic) Sequence at http://www.sanger.ac.uk/cgi-bin/blast/submitblast/s_zooepidemicus incomplete last accessed on Jul. 01, 2008 | Currently on contig GZOO 1414 1396-1a02.w2k1396 residues 29648-31387 | Currently on contig J25443Df01.p1k Residues 384986-386020 | Currently on contig J25443Df01.p1k Residues 11359-12639 | Currently on contig zoo122a01.p1k residues 171841-172932 |
| *S. pyogenes* (beta-haemolytic) Sequence at http://www.sanger.ac.uk/Projects/S_pyogenes/ | Residues 226656-227440 | Residues 582244-583280 | Residues 1097957-1099241 | Residues 1756634-1757727 |
| *S. uberis* http://www.sanger.ac.uk/Projects/S_uberis/ | Residues 147388-148092 | NONE | Residues 995140-996400 | Residues 1764212-1765308 |

TABLE 7A-continued

| most preferred genes and homologues | | | | |
|---|---|---|---|---|
| *S. pneumoniae* http://www.sanger.ac.uk/ Projects/S_pneumoniae/23F/ | NONE | Residues 1312069-1312660 | Residues 1048493-1049757 | Residues 1901125-1902171 |
| *S. agalactieae* NC_007432 | ref\|YP_329152.1\| | ref\|YP_330019.1\| | ref\|YP_329756.1\| | ref\|YP_330622.1\| |
| *S. suis* http://www.sanger.ac.uk/ Projects/S_suis/ | NONE | NONE | Residues 888290-889588 | 67730-68754 |
| *S. iniae* (beta-haemolytic) http://www.hgsc.bcm.tmc.edu/ bcm/blast/microbialblast.cgi Last searched on Jul. 25, 2007 | NONE | NONE | NONE | contig 00203 residues 18147-19153 |

TABLE 7B other preferred genes and homologues

| Bacterium | Disease in animals | Disease in humans | slaA | seeI |
|---|---|---|---|---|
| *S. equi* (beta-haemolytic) | Strangles in horses. | None | 0 Also has second homologue virtually identical to the one found in zooepidemicus 5.7e−105 824084-824656 | 0 |
| *S. zooepidemicus* (beta-haemolytic) Sequence at http://www.sanger.ac.uk/ cgi-bin/blast/submitblast/ s_zooepidemicus | Abortion, mastitis, keratitis, wound infections, abscesses in a wide variety of animals. | Nephritis, meningitis | Contig zoo122a01.p1k Residues 175312-175881 | NONE |
| *S. pyogenes* (beta-haemolytic) Sequence at http://www.sanger.ac.uk/ Projects/S_pyogenes 29/11/07/ | None. | Necrotising facititis, pharyngitis, sepsis. | NONE in Manfredo This is present in M2, M3, M6, M28 strains and phage PhiNIH1.1at the NCBI 1e−111 | 6.6e−167 Residues 1031237-1032011 |

| Bacterium | seeH | seeL | seeM | slaB |
|---|---|---|---|---|
| *S. equi* (beta-haemolytic) | 0 | 0 | 0 | 0 |
| *S. zooepidemicus* (beta-haemolytic) Sequence at http://www.sanger.ac.uk/ cgi-bin/blast/submitblast/ s_zooepidemicus | NONE | NONE | NONE | Contig zoo122a01.p1k Residues 175312-175881 |
| *S. pyogenes* (beta-haemolytic) Sequence at http://www.sanger.ac.uk/ Projects/S_pyogenes 29/11/07/ | 1.8e−148 Residues 204328-204943 | NONE in Manfredo Present in various pyogenes strains at NCBI 1e−131 | NONE in Manfredo Present in various pyogenes strains at NCBI 1e−125 | NONE in Manfredo This is present in M2, M3, M6, M28 strains and phage PhiNIH1.1at the NCBI 4e−72 |

TABLE 8 other preferred strains

| Bacterium | Disease in animals | Disease in humans |
|---|---|---|
| *S. canis* (beta-haemolytic) | Streptococcal toxic shock syndrome in dogs.. Respiratory infection, toxic shock, sepsis in cats | urinary infection soft tissue infection, bacteremia, pneumonia, bone infection |
| *S. dysgalactiae* subsp *dysgalactae* | Mastitis in cattle, | |
| *S. dysgalactiae* subsp *equisimilis* (beta-haemolytic) | septicemia in dogs Respiratory disease in horses | Respiratory, tissue infections, cellulitis, septicemia. |

TABLE 8-continued other preferred strains

| Bacterium | Disease in animals | Disease in humans |
|---|---|---|
| *S. porcinus* (beta-haemolytic) | Lymphadenitis in pigs, abscessation primarily of the head and neck lymph nodes, Abortion | Abortion |

REFERENCES

Alexander, J. E., Andrew, P. W., Jones, D. & Roberts, I. S. (1993) Characterization of an aromatic amino acid-dependent *Listeria monocytogenes* mutant: attenuation, persistence, and ability to induce protective immunity in mice. Infect Immun. 61 2245-8.

Artiushin, S. C., Timoney, J. F., Sheoran, A. S., Muthupalani, S. K. (2002). Characterization and immunogenicity of pyrogenic mitogens SePE-H and SePE-I of *Streptococcus equi*. Microbial Pathogenesis 32 71-85. Bazeley, P. L. (1940) Experimental immunity to *Str. equi*. Austr. Vet. J. 16: 243-259.

Bazeley, P. L. (1942) Vaccination against strangles. Austr. Vet. J. 18: 141-155.

Beres, S. B., Sylva, G. L., Barbian, K. D., Lei, B., Hoff, J. S., Mammarella, N. D., Liu, M. Y., Smoot, J. C., Porcella, S. F., Parkins, L. D., Campbell, D. S., Smith, T. M., McCormick, J. K., Leung, D. Y., Schlievert, P. M., Musser, J. M. (2002). Genome sequence of a serotype M3 strain of group A *Streptococcus*: phage-encoded toxins, the high-virulence phenotype, and clone emergence. Proc Natl Acad Sci USA 99 10078-83.

Betschel, S. D., Borgia, S. M., Barg, N. L., Low, D. E. & De Azavedo, J. C. (1998) Reduced virulence of group A streptococcal Tn916 mutants that do not produce streptolysin S. Infect Immun. 66 1671-9.

Chamberlain, L. M., Strugnell, R., Dougan, G., Hormaeche, C. E. & Demarco de Hormaeche, R. (1993) *Neisseria gonorrhoeae* strain MS11 harbouring a mutation in gene aroA is attenuated and immunogenic. Microb Pathog. 15 51-63.

Chanter, N., Ward, C. L., Talbot, N. C., Flanagan, J. A., Binns, M., Houghton, S. B., Smith, K. C. & Mumford, J. A. (1999) Recombinant hyaluronate associated protein as a protective immunogen against *Streptococcus equi* and *Streptococcus zooepidemicus* challenge in mice. Microb Pathog 27 133-43.

Chanter, N., Talbot, N. C., Newton, J. R., Hewson, D. & Verheyen, K. (2000) *Streptococcus equi* with truncated M-proteins isolated from outwardly healthy horses. Microbiology 146 1361-9.

Dougherty, B. A. & van de Rijn, I. (1994) Molecular characterization of hasA from an operon required for hyaluronic acid synthesis in group A streptococci. J Biol. Chem. 269 169-75.

Galan, J. E. & Timoney, J. F. (1985) Immune complexes in purpura hemorrhagica of the horse contain IgA and M antigen of *Streptococcus equi*. J. Immunol. 135 3134-7.

Harrington, D. J., Sutcliffe, I. C. & Chanter, N. (2002) The molecular basis of *Streptococcus equi* infection and disease. Microbes Infect. 4 501-10.

Hamlen, H. J., Timoney, J. F., Bell, R. J. 1994. Epidemiological and immunologic characteristics of *Streptococcus equi* infection in foals. Journal of the American Veterinary Medical Association 204, 768-75.

Hamilton A, Robinson C, Sutcliffe I C, Slater J, Maskell D J, Davis-Poynter N, Smith K, Waller A, Harrington D J. Mutation of the maturase lipoprotein attenuates the virulence of *Streptococcus equi* to a greater extent than does loss of general lipoprotein lipidation. Infect Immun. 2006 December; 74(12):6907-19.

Hartford, O. M., Foster, T. J. & Jacobs, A. A. C. (1999) *Streptococcus equi* vaccine. U.S. Pat. No. 5,895,654. Appl. No.: 789727. Filed: Jan. 27, 1997.

Herwald H, Cramer H, Morgelin M, Russell W, Sollenberg U, Norrby-Teglund A, Flodgaard H, Lindbom L, Bjorck L. (2004) M protein, a classical bacterial virulence determinant, forms complexes with fibrinogen that induce vascular leakage. Cell. 116:367-79.

Ingham, A., Zhang, Y. & Prideaux, C. (2002) Attenuation of *Actinobacillus pleuropneumoniae* by inactivation of aroQ. Vet Microbiol. 84 263-73.

Izhar, M., DeSilva, L., Joysey, H. S. & Hormaeche, C. E. (1990) Moderate immunodeficiency does not increase susceptibility to *Salmonella typhimurium* aroA live vaccines in mice. Infect Immun. 58 2258-61.

Jacobs, A. A., Goovaerts, D., Nuijten, P. J., Theelen, R. P., Hartford, O. M. & Foster, T. J. (2000) Investigations towards an efficacious and safe strangles vaccine: submucosal vaccination with a live attenuated *Streptococcus equi*. Vet Rec 147 563-7.

Jorm, L. R. (1990) Strangles in horse studs: incidence, risk factors and effect of vaccination. Aust Vet J. 67 436-9.

Karnell, A., Sweiha, H. & Lindberg, A. A. (1992) Auxotrophic live oral *Shigella flexneri* vaccine protects monkeys against challenge with *S. flexneri* of different serotypes. Vaccine. 10 167-74.

Kelly, C., Bugg, M., Robinson, C., Mitchell, Z., Davis-Poynter, N., Newton, J. R., Jolley, K. A., Maiden, M. C., Waller, A. S. 2006. Sequence variation of the SeM gene of *Streptococcus equi* allows discrimination of the source of strangles outbreaks. Journal of Clinical Microbiology 44, 480-6.

Kemp-Symonds J, Kemble T, Waller A. Modified live *Streptococcus equi* ('strangles') vaccination followed by clinically adverse reactions associated with bacterial replication. Equine Vet J. 2007 May; 39(3):284-6.

Kwaga, J. K., Allan, B. J., van der Hurk, J. V., Seida, H. & Potter, A. A. (1994) A carAB mutant of avian pathogenic *Escherichia coli* serogroup O2 is attenuated and effective as a live oral vaccine against colibacillosis in turkeys. Infect Immun. 62 3766-72.

Maguin, E., Duwat, P., Hege, T., Ehrlich, D. & Gruss, A. (1992) New thermosensitive plasmid for gram-positive bacteria. J Bacteriol 174 5633-8.

Meehan, M., Nowlan, P. & Owen, P. (1998) Affinity purification and characterization of a fibrinogen-binding protein complex which protects mice against lethal challenge with *Streptococcus equi* subsp. *equi*. Microbiology. 144 993-1003. Meehan, M. & Muldowney, D. A., Watkins, N. J., Owen, P. (2000) Localization and characterization of the ligand-binding domain of the fibrinogen-binding protein (FgBP) of *Streptococcus equi* subsp. *equi*. Microbiology. 146 1187-94.

Meehan, M., Lynagh, Y., Woods, C. & Owen, P. (2001) The fibrinogen-binding protein (FgBP) of *Streptococcus equi* subsp. *equi* additionally binds IgG and contributes to virulence in a mouse model. Microbiology. 147 3311-22.

Newland, J. W., Hale, T. L. & Formal, S. B. (1992) Genotypic and phenotypic characterization of an aroD deletion-attenuated *Escherichia coli* K12-*Shigella flexneri* hybrid vaccine expressing *S. flexneri* 2a somatic antigen. Vaccine. 10 766-76.

Newton, J. R., Wood, J. L., Dunn, K. A., DeBrauwere, M. N. & Chanter, N. (1997) Naturally occurring persistent and asymptomatic infection of the guttural pouches of horses with *Streptococcus* equi. Vet Rec 140 84-90.

Newton, J. R., Verheyen, K., Talbot, N. C., Timoney, J. F., Wood, J. L., Lakhani, K. H. & Chanter, N. (2000) Control of strangles outbreaks by isolation of guttural pouch carriers identified using PCR and culture of *Streptococcus equi*. Equine Vet J 32 515-26.

Proft, T., Webb, P. D., Handley, V., Fraser, J. D. (2003). Two novel superantigens found in both group A and group C *Streptococcus*. Infection and Immunity 71 1361-9. Pusterla, N., Watson, J. L., Affolter, V. K., Magdesian, K. G., Wilson, W. D. & Carlson, G. P. (2003) Purpura haemorrhagica in 53 horses. Vet Rec. 153 118-21.

Sheoran, A. S., Artiushin, S. & Timoney, J. F. (2002) Nasal mucosal immunogenicity for the horse of a SeM peptide of *Streptococcus equi* genetically coupled to cholera toxin. Vaccine 20 1653-9.

Simmons, C. P., Hodgson, A. L. & Strugnell, R. A. (1997) Attenuation and vaccine potential of aroQ mutants of *Corynebacterium pseudotuberculosis*. Infect Immun. 65 3048-56.

Stocker, B. A. (1990) Aromatic-dependent *Salmonella* as live vaccine presenters of foreign epitopes as inserts in flagellin. Res Microbiol. 141 787-96.

Sweeney, C. R., Timoney, J. F., Newton, J. R., Hines, M. T. 2005. *Streptococcus equi* infections in horses: guidelines for treatment, control, and prevention of strangles. Journal of Veterinary Internal Medicine 19, 123-34.

Tao, L., Hollingshead, S. K., Suvorov, A. N., Ferretti, J. J. & McShan, W. M. (1995) Construction of a *Streptococcus pyogenes* recA mutant via insertional inactivation, and cloning and sequencing of the complete recA gene. Gene. 162 59-62.

Timoney, J. F. & Eggers, D. (1985) Serum bactericidal responses to *Streptococcus equi* of horses following infection or vaccination. Equine Vet J. 17 306-10.

Timoney, J. F. (1993a) Strangles. Vet Clin North Am Equine Pract 9 365-374.

Timoney, J. F. (1993b) Protection of equines against *Streptococcus equi*. U.S. Pat. No. 5,183,659 Appl. No.: 207320 Filed: Jun. 15, 1988.

Timoney, J. F., Artiushin, S. C. & Boschwitz, J. S. (1997) Comparison of the sequences and functions of *Streptococcus equi* M-like proteins SeM and SzPSe. Infect Immun 65 3600-5.

Todd, A. G. 1910. Strangles. Journal of Comparative Pathology and Therapeutics 23, 212-29.

Vaughan, L. M., Smith, P. R. & Foster, T. J. (1993) An aromatic-dependent mutant of the fish pathogen *Aeromonas salmonicida* is attenuated in fish and is effective as a live vaccine against the salmonid disease furunculosis. Infect Immun. 61 2172-81.

Walker, J. A. & Timoney, J. F. (2002) Construction of a stable non-mucoid deletion mutant of the *Streptococcus equi* Pinnacle vaccine strain. Vet Microbiol. 89 311-21.

Waller A, Flock M, Smith K, Robinson C, Mitchell Z, Karlstrom A, Lannergard J, Bergman R, Guss B, Flock J I. Vaccination of horses against strangles using recombinant antigens from *Streptococcus equi*. Vaccine. 2007 May 4; 25(18):3629-35.

Waller, A., Dudgeon, T., Hars, J., Johnson, I. & Czaplewski, L. G. (2001) A whole genome approach for validation of metalloenzyme targets to discover novel class antibiotics. 41st ICAAC Poster F-2122.

Wessels, M. R., Goldberg, J. B., Moses, A. E. & DiCesare, T. J. (1994) Effects on virulence of mutations in a locus essential for hyaluronic acid capsule expression in group A streptococci. Infect Immun. 62 433-41.

Woolcock, J. B. (1975) Immunity to *Streptococcus equi*. Aust Vet J. 51 554-9.

http://www.biosafety.be/EMEA/Table_EquilisStrepT.htm http://www.sangerac.uk/Projects/S_equi/ http://www.wyethah.ca/wyeth_equine/pinnacle.html

Sequence Annexes 1-6

WT ATGTTACAATTTGCTTCAAATATTTTAGCTACTAGTGTAGCAGAAACAACTCAAGTTGCTCCTGGTGGTTGCTGCTGTTG (SEQ ID NO: 1)
SHMAPR ATGTTACAATTTGCT----------------------------------------------------------------- (SEQ ID NO: 2)

WT CTGTTCTTGTTGTTGCTGCGTCTCAGCTTCATGGGGCAATACTACCATAAACAACAATTATGGTGCAGCTGAGCCAAAAG
SHMAPR -------------------------------------------------------------*AAGCTT*GCTGAGCCAAAAG

WT CGTAA
SHMAPR CGTAA

The HindIII restriction site used to generate the deletion construct is shown in italics.

WT ATGAGAACATTAAAAAACCTCATAACTGTTGTGGCCTTTAGTATTTTTTGGGTACTGTTGATTTACGTCAATGTTTATCT (SEQ ID NO: 3)
SHMAPR ATGAGAACATTAAAAAACCTCATAACTGTTGTGGCCTTTAGTATTTTTTGGGTACTGTTGATTTACGTCAATGTTTATCT (SEQ ID NO: 4)

WT CTTTGGTGCTAAAGGAAGCTTGTCAATTTATGGCTTTTTGCTGATAGCTTATCTATTAGTCAAAATGTCCTTATCTTTTT
SHMAPR CTTTGGTGCTAAAGGAAGCTTGTCAATTTATGGCTTTTTGCTGATAGCTTATCTATTAGTCAAAATGTCCTTATCTTTTT

WT TTTACAAGCCATTTAAGGGAAGGGCTGGGCAATATAAGGTTGCAGCCATTATTCCCTCTTATAACGAAGACGCTGAGTCA
SHMAPR TTTACAAGCCATTTAAGGGAAGGGCTGGGCAATATAAGGTTGCAGCCATTATTCCCTCTTATAACGAAGACGCTGAGTCA

WT TTGCTAGAGACCTTAAAAAGTGTTCAGCAGCAAACCTATCCCCTAGCAGAAATTTATGTTGTTGACGATGGAAGTGCTGA
SHMAPR TTGCTAGAGACCTTAAAAAGTGTTCAGCAGCAAACCTATCCCCTAGCAGAAAT---------------------------

WT TGAGACAGGTATTAAGCGCATTGAAGACTATGTGCGTGACACTGGTGACCTATCAAGCAATGTCATTGTTCATCGGTCAG
SHMAPR --------------------------------------------------------------------------------

WT AGAAAAATCAAGGAAAGCGTCATGCACAGGCCTGGGCCTTTGAAAGATCAGACGCTGATGTCTTTTTGACCGTTGACTCA
SHMAPR --------------------------------------------------------------------------------

WT GATACTTATATCTACCCTGATGCTTTAGAGGAGCTGTTAAAGACCTTTAATGACCCAACTGTTTTTGCTGCGACGGGTCA
SHMAPR --------------------------------------------------------------------------------

WT CCTTAATGTCAGAAATAGACAAACCAATCTCTTAACACGCTTGACAGATATTCGCTATGATAATGCTTTTGGCGTTGAAC
SHMAPR --------------------------------------------------------------------------------

WT GAGCTGCCCAATCAGTTACGGGTAATATCCTTGTTTGCTCAGGCCCACTTAGCGTTTACAGACGCGAGGTGGTTGTTCCT
SHMAPR --------------------------------------------------------------------------------

-continued

WT AATATAGACAGATACATCAACCAGACCTTCCTGGGTATTCCTGTAAGTATCGGTGATGACAGGTGCTTGACCAACTATGC
SHMAPR --------------------------------------------------------------------------------

WT AACTGATTTAGGAAAGACTGTTTATCAATCCACTGCTAAATGTATTACAGATGTTCCTGACAAGATGTCTACTTACTTGA
SHMAPR --------------------------------------------------------------------------------

WT AGCAGCAAAACCGCTGGAACAAGTCCTTCTTTAGAGAGTCCATTATTTCTGTTAAGAAAATCATGAACAATCCTTTTGTA
SHMAPR --------*GATATC*TGGAACAAGTCCTTCTTTAGAGAGTCCATTATTTCTGTTAAGAAAATCATGAACAATCCTTTTGTA

WT GCCCTATGGACCATACTTGAGGTGTCTATGTTTATGATGCTTGTTTATTCTGTGGTGGATTTCTTTGTAGGCAATGTCAG
SHMAPR GCCCTATGGACCATACTTGAGGTGTCTATGTTTATGATGCTTGTTTATTCTGTGGTGGATTTCTTTGTAGGCAATGTCAG

WT *AGAATTTGATTGGCT*CAGGGTTTTAGCCTTTCTGGTGATTATCTTCATTGTTGCTCTTTGTCGGAACATTCATTACATGC
SHMAPR AGAATTTGATTGGCTCAGGGTTTTAGCCTTTCTGGTGATTATCTTCATTGTTGCTCTTTGTCGGAACATTCATTACATGC

WT TTAAGCACCCGCTGTCCTTCTTGTTATCTCCGTTTTATGGGGTGCTGCATTTGTTTGTCCTACAGCCCTTGAAATTGTAT
SHMAPR TTAAGCACCCGCTGTCCTTCTTGTTATCTCCGTTTTATGGGGTGCTGCATTTGTTTGTCCTACAGCCCTTGAAATTGTAT

WT TCTCTTTTTACTATTAGAAATGCTGACTGGGGAACACGTAAAAAATTATTATAA
SHMAPR TCTCTTTTTACTATTAGAAATGCTGACTGGGGAACACGTAAAAAATTATTATAA

The EcoRV restriction site used to generate the deletion construct is shown in italics.

WT ATGTTTTTGAGAAATAACAAGCAAAAATTTAGCATCAGAAAACTAAGTGCCGGTGCAGCATCAGTATTAGTTGCAACAAG(SEQ ID NO: 5)
SHMAPR ATGTTTTTGAGAAATAACAAGCAAAAATTTAGCATCAGAAAACTAAGTGCCGGTGCAGCATCAGTATTAGTTGCAACAAG(SEQ ID NO: 6)

WT TGTGTTGGGAGGGACAACTGTAAAAGCGAACTCTGAGGTTAGTCGTACGGCGACTCCAAGATTATCGCGTGATTTAAAAA
SHMAPR TGTGTTGGGAGGGACAACTGTAAAAGCGAACTCTGAGGTTAGTCGTACGGCGACTCCAAGATTATCGCGTGATTTAAAAA

WT ATAGATTAAGCGAAATAGCCATAAGTAGAGATGCCTCATCAGCCCAAAAAGTTCGAAATCTTCTAAAAGGCGCCTCTGTT
SHMAPR ATAGATTAAGCGAAATAGCCATAAGTAGAGATGCCTCATCAGCCCAAAAAGTTCGAAATCTTCTAAAAGGCGCCTCTGTT

WT GGGGATTTACAGGCATTATTGAGAGGTCTTGATTCAGCAAGGGCTGCGTATGGTAGAGATGATTATTACAATTTATTGGT
SHMAPR GGGGATTTACAGGCATTATTGAGAGGTCTTGATTCAGCAAGGGCTGCGTATGGTAGAGATGATTATTACAATTTATTGGT

WT GCACCTTTCATCGATGTTAAATGATAAACCTGATGGGGATAGAAGACAATTAAGTTTGGCTTCATTACTTGTAGATGAAA
SHMAPR GCACCTTCCATCGATGTAAAAT*GATATC*----------------------------------------------------

WT TTGAAAAGCGGATTGCTGATGGAGATAGTTATGCAAAACTTCTTGAGGCTAAACTTGCAGCTATTAAATCTCAACAAGAA
SHMAPR --------------------------------------------------------------------------------

WT ATGCTTAGAGAAAGAGATTCCCAACTTCGAAATCTAGAGAAGGAAAAAGAACAAGAACTACAAAAAGCTAAAGATGAGCG
SHMAPR --------------------------------------------------------------------------------

WT TCAAGCTCTTACCGAATCATTCAACAAAACTTTATCAAGATCAACAAAAGAGTATAATAAACTAAAAACAGAACTTGCAA
SHMAPR --------------------------------------------------------------------------------

WT AAGAAAAAGAAAAAGCAGCTAAGATGACTAAGGAATTAGCAGATAAGCTAAGCAATGCTGAAGCAAGTCGTGATAAAGCC
SHMAPR --------------------------------------------------------------------------------

WT TTTGCAGTATCAAAAGATTTAGCAGATAAACTAAGTAGTGCTGAAGCAAGTCGTGATAAAGCTTTTGCAGTATCAAAAGA
SHMAPR --------------------------------------------------------------------------------

WT TTTAGCAGATAAATTGGCAGCTAAAACAGCAGAAGCTGAAAAGTTAATGGAAAACGTTGGTAGTCTAGACCGCTTGGTAG
SHMAPR --------------------------------------------------------------------------------

WT AGTCTGCAAAACGTGAAATGGCTCAAAAATTAGCAGAAATTGATCAATTAACTGCTGATAAGGCTAAGGCTGATGCAGAG
SHMAPR --------------------------------------------------------------------------------

WT CTTGCAGCTGCAAATGACACCATTGCATCACTTCAAACAGAGCTAGAAAAAGCTAAGACAGAGCTTGCTGTTTCAGAGCG
SHMAPR --------------------------------------------------------------------------------

WT TTTGATTGAATCAGGCAAACGTGAAATTGCTGAGCTACAAAAACAAAAAGATGCTTCTGATAAGGCTTTAGTAGAATCAC
SHMAPR --------------------------------------------------------------------------------

WT AAGCTAATGTAGCAGAGCTTGAAAAACAAAAAGCAGCATCAGATGCTAAGGTAGCAGAGCTTGAAAAAGAAGTTGAAGCT
SHMAPR --------------------------------------TGAGATGCTAAGGTAGCAGAGCTTGAAAAAGAAGTTGAAGCT

WT GCTAAAGCTGAGGTTGCAGATCTTAAAGTACAATTAGCTAAGAAAGAAGAAGAGCTTGAAGCCGTTAAGAAGGAAAAAGA
SHMAPR GCTAAAGCTGAGGTTGCAGATCTTAAAGTACAATTAGCTAAGAAAGAAGAAGAGCTTGAAGCCGTTAAGAAGGAAAAAGA

WT AGCGCTTGAAGCTAAGATTGAAGAGCTCAAAAAAGCTCATGCTGAGGAACTTTCAAAACTTAAAGAAATGCTTGAGAAGA
SHMAPR AGCGCTTGAAGCTAAGATTGAAGAGCTCAAAAAAGCTCATGCTGAGGAACTTTCAAAACTTAAAGAAATGCTTGAGAAGA

WT AAGACCATGCAAATGCAGATCTTCAAGCAGAAATCAATCGCTTGAAGCAAGAGCTAGCTGACAGGATTAAGTCATTGTCA
SHMAPR AAGACCATGCAAATGCAGATCTTCAAGCAGAAATCAATCGCTTGAAGCAAGAGCTAGCTGACAGGATTAAGTCATTGTCA

-continued

WT CAAGGTGGTCGTGCTTCACAAACAAACCCAGGCACTACAACTGCTAAAGCAGGTCAATTGCCATCTACTGGTGAGTCTGC<br>
SHMAPR CAAGGTGGTCGTGCTTCACAAACAAACCCAGGCACTACAACTGCTAAAGCAGGTCAATTGCCATCTACTGGTGAGTCTGC

WT TAACCCATTCTTCACTATTGCAGCTCTTACTGTCATCGCTGGTGCTGGTATGGCTGTGGTGTCTCCTAAACGCAAAGAAA<br>
SHMAPR TAACCCATTCTTCACTATTGCAGCTCTTACTGTCATCGCTGGTGCTGGTATGGCTGTGGTGTCTCCTAAACGCAAAGAAA

WT ACTAA<br>
SHMAPR ACTAA

The seM deletion generated two stop codons (underlined), which would abolish cell surface binding of the truncated SeM product.

The EcoRV restriction site used to generate the deletion construct is shown in italics.

WT ATGACACAAACACTTCAGGTTAAGTCTCGTATCAATGACTATCCGATTATCTTTACAGACGATATTTTTCAGCCGCTGAA(SEQ ID NO: 7)<br>
SHMAPR ATGACACAAACACTTCAGGTTAAGTCTCGTATCAATGACTATCC------------------------------------(SEQ ID NO: 8)

WT TCAATTTCTTGCTGAAAAAGGAGACGTCAAGCTATTATTTATCACTGATCAAACGGTATTTGATTTATACCAGCCTTTAT<br>
SHMAPR --------------------------------------------------------------------------------

WT TTAGACGTTTTCAACAGGATTACGATAGTTACCTTCATATTGCTGCTCCAGGGGGGCAATCTAAGTCTCTAGAGGAGGTT<br>
SHMAPR --------------------------------------------------------------------------------

WT AGTCGGATTTACGATCGACTGATTAGGGCTAATTTTTCTAAAAAGGACGTCATTGTTACTGTTGGAGGAGGGGTGATTGG<br>
SHMAPR

WT AGATCTTGGGGGATTTGTTGCGGCAACCTTTTACCGCGGGATTTCCTACGTTCAGATTCCAACAACCTTACTTAGTCAGG<br>
SHMAPR --------------------------------------------------------------------------------

WT TAGACAGCAGCATTGGTGGTAAGGTTGGGGTTCACTTTAAGGGCTTGACCAATATGATAGGCAGTATCTACCCTCCAAAC<br>
SHMAPR --------------------------------------------------------------------------------

WT CAGATTATCGTGTCAGCCAAGTTTTTAGACACGCTTTCTGAAAGAGAATTTGCCTGCGGCATCAGCGAAATGATTAAAAT<br>
SHMAPR --------------------------------------------------------------------------------

WT TGGTTTTATTCATGATCGCAAGCTCTTTCAACAGCTCCTAGCCTTCCCCAAGGACCGCAATCAAGAGCAGCTCAGGCAAA<br>
SHMAPR --------------------------------------------------------------------------------

WT TGATTTTTCAAGCGATTTGCCATAAAAAAAGAGTGGTTGAAAAGGATGAATTTGAAGGCAATCTCCGCATGTCCTTAAAT<br>
SHMAPR --------------------------------------------------------------------------------

WT TTCGGGCATACGCTAGGGCATGCGATTGAAGCCTTATGCCATCACGAGCTTTACAGGCATGGTGAGGCTATTGCGATTGG<br>
SHMAPR --------------------------------------------------------------------------------

WT CATGGTCTTTGAGGCCAAGCTGGCCGTCCAGCAGCAGCTATTGAGCCAACAGGATTTAGAGGCATTACAGGCTGCCTTTG<br>
SHMAPR --------------------------------------------------------------------------------

WT AGGCTTATCAGCTACCTACCACACTTGAGGCTAAGTCAATGACAGCCGAAGCCTTGATGACTGTTTTAAAAACAGATAAG<br>
SHMAPR --------------------------------------------------------------------------------

WT AAAAATTCTGGTCAGCATATTGTCCTCATTTTGCCAACGACAAAAGGCTATGTAAGCTTTCCTATTGCTAAGCATGACAG<br>
SHMAPR --------------------------------------------------------------------------------

WT TCGCCTGCTGGATTGGCTAAGAA*GCCTGCTAGATATCGCCTGA*<br>
SHMAPR ------------------------------*GATATC*GCCTGA

The EcoRV restriction site used to generate the deletion construct is shown in italics.

(SEQ ID NO: 9)<br>
WT ATGATATCAGGGATCAAGACAGTTACGTCCGATATGTCAAGCAAAACAAATAATCACTGCCTAGATAAATCAGAAATTGC<br>
(SEQ ID NO: 10)<br>
SHMAPR ATGATATCAGGGATCAAGACAGTTACGTCCGATATGTCAAGCAAAACAAATAATCACTGCCTAGATAAATCAGAAATTGC

WT TAGGGTTATGCTTGATTATCCTGATAAGCAGATAAGTAGATTTGACATAGGAGGGGTCATGTTATTAATTAAAAATGGGC<br>
SHMAPR TAGGGTTATGCTTGATTATCCTGATAAGCAGATAAGTAGATTTGACATAGGAGGGGTCATGTTATTAATTAAAAATGGGC

WT GTGTGATGGATCCAAAATCACAGCTAGATCAGGTGGCAGATGTCTTAATTGATAATGGAAGGATTTTACGGATTGCTCCA<br>
SHMAPR GTGTGATGGATCCAAAATCACAGCTAGATCAGGTGGC*AAGCTT*-------------------------------------

WT GACATTGAGCATGATGAGGTAGAGCAGATCGATGCCAGTGGACTTGTTGTTGCTCCTGGTTTAGTGGATATTCATGTTCA<br>
SHMAPR --------------------------------------------------------------------------------

WT TTTTAGAGAGCCGGGTCAAACGCACAAGGAGGACATTCATACAGGTGCTCTGGCAGCAGCTGCTGGTGGGGTGACAACAG<br>
SHMAPR --------------------------------------------------------------------------------

-continued

WT     TAGTCATGATGGCAAACACCAATCCTGTTATATCAGATACGGAAACCTTACAGGCTGTTCTAGCAAGTGCTGCTAAAGAA
SHMAPR --------------------------------------------------------------------------------

WT     AAAATTAACATTTATACCAATGCTAGTGTGACCAAGCGGTTCAATGGCCAAGAGCTAACAGACTTTAAAGCGCTCTTAGC
SHMAPR --------------------------------------------------------------------------------

WT     AGCTGGTGCGGTCAGTTTTTCTGATGATGGCATTCCTTTAGAGAGCTCCAAGGTCTTAAAGGAAGCATTGGATTTGGCTA
SHMAPR --------------------------------------------------------------------------------

WT     AGGCCAACAAGACCTTCATTGCCCTGCATGAGGAGGATCCCCAATTAAACGGTGTCCTTGGCTTCAATGAGCATATCGCT
SHMAPR --------------------------------------------------------------------------------

WT     AAGGATCATTTTCATTTTTGTGGCGCTACTGGTGTGGCAGAATATAGTATGATTGCCAGAGATGTGATGATTGCCTATGA
SHMAPR --------------------------------------------------------------------------------

WT     TCGACAAGCTCATGTTCATATTCAACATTTATCTAAGGCTGAGTCTGTTAAGGTAGTTGCCTTTGCTCAGCAGTTAGGTG
SHMAPR --------------------------------------------------------------------------------

WT     CCAAGGTCACAGCCGAGGCAACACCGCAGCATTTTTCTAAAACAGAAGACCTTTTACGGCTTGCAGGGGCAAATGCCAAG
SHMAPR --------------------------------------------------------------------------------

WT     ATGAATCCGCCTCTAAGAACAGAACAAGATAGATTAGCAGTTATTGAGGGGCTCAAATCAGGTGTCATAGCTATTATTGC
SHMAPR --------------------------------------------------------------------------------

WT     AACGGATCATGCACCACATCATCGTGATGAAAAGGCCGTTGCTGATCTGACCAAGGCACCATCTGGAATGACCGGCTTAG
SHMAPR --------------------------------------------------------------------------------

WT     AAACCTCATTGTCATTAGGCCTGACAAATCTTGTGGAGCCGAGCCATCTTTCATTGATGGCGTTATTAGAGAAAATGACC
SHMAPR --------------------------------------------------------------------------------

WT     ATTAATCCAGCCTCACTATATAGCTTTGATGCTGGTTATTTGGCTGAGTCTGGCCCTGCTGATCTTGTTATTTTTGCTGA
SHMAPR --------------------------------------------------------------------------------

WT     CAAGGAGGAGCGTTTGGTAACAGAAGCCTTTGCTTCAAAGGCTAGTAATTCACCTTTTATTGGCGAAACCCTAAAGGGAG
SHMAPR --------AGCGTTTGGTAACAGAAGCCTTTGCTTCAAAGGCTAGTAATTCACCTTTTATTGGCGAAACCCTAAAGGGAG

WT     TTGTGAAATACACCATTGCTAAGGGACAAATTGTTTATCAGGCAGACAACTAA
SHMAPR TTGTGAAATACACCATTGCTAAGGGACAAATTGTTTATCAGGCAGACAACTAA

The HindIII restriction-
site used to generate the deletion construct is shown in italics.

(SEQ ID NO: 11)
WT     TTGGCAAAAAAAGTTAAAAAAAATGAAGAAATCACCAAAAAATTTGGTGATGAACGTCGTAAAGCACTTGATGATGCGTT
(SEQ ID NO: 12)
SHMAPR TTGGCAAAAAAAGTTAAAAAAAATGAAGAAATCACCAAAAAATTTGGTGATGAACGTCGTAAAGCACTTGATGATGCGTT

WT     AAAGAACATCGAAAAAGATTTTGGTAAGGGTGCGGTTATGCGCCTTGGTGAGCGTGCAGAGCAAAAGGTTCAGGTGATGA
SHMAPR AAAGAACATCGAAAAAGATTTTGGTAAGGGTGCGGTTATGCGCCTTGGTGAGCGTGCAGAGCAAAAGGTTCAGGTGATGA

WT     GTTCAGGCAGTCTTGCTTTAGACATTGCGCTTGGAGCAGGTGGCTATCCTAAAGGGCGTATTATTGAAATCTATGGACCA
SHMAPR GTTCAGGCAGTCTTGCTTTAGACATTGCGCTTGGAGCAGGTGGCTATCCTAAAGGGCGTATTATTGAAATCTATGGACCA

WT     GAGTCTTCTGGTAAAACAACAGTTGCCCTGCATGCAGTAGCGCAGGCTCAAAAAGAAGGTGGTATTGCAGCCTTCATTGA
SHMAPR GAGTCTTCTGGTAAAACAACAGTTGCCCTGCATGCAGTAGCGCAGGCTCAAAAAGAAGGTGGTATTGCAGCCTT------

WT     TGCGGAGCATGCCTTGGACCCTGCTTATGCTGCGGCGCTGGGTGTTAATATTGATGAGCTGCTTTTGTCACAGCCGGATT
SHMAPR --------------------------------------------------------------------------------

WT     CTGGTGAGCAAGGACTTGAGATAGCAGGTAAACTGATTGATTCTGGTGCTGTTGATTTGGTTGTTGTCGACTCTGTTGCA
SHMAPR --------------------------------------------------------------------------------

WT     GCTCTAGTGCCTCGTGCTGAGATTGATGGTGATATTGGTGATAACCATGTTGGCTTGCAGGCTCGTATGATGAGTCAGGC
SHMAPR --------------------------------------------------------------------------------

WT     GATGCGTAAGCTTTCAGCCTCAATCAATAAAACCAAGACAATTGCGATCTTTATTAACCAGCTGCGTGAAAAGGTAGGGG
SHMAPR --------------------------------------------------------------------------------

WT     TTATGTTTGGTAATCCAGAGACGACACCAGGTGGTCGTGCTTTGAAATTCTATGCCTCTGTCCGTCTGGATGTTCGTGGA
SHMAPR --------------------------------------------------------------------------------

WT     ACAACACAAATAAAAGGAACTGGAGATCAAAAAGACAGTAGTATTGGTAAGGAAACCAAGATTAAGGTTGTTAAGAATAA
SHMAPR --------------------------------------------------------------------------------

WT     GGTTGCTCCGCCATTTAAGGTGGCTGAGGTTGAAATCATGTATGGAGAAGGCATCTCACGTACAGGTGAGCTGATTAAAA
SHMAPR ----------------------------------------*GATATC*GAAGGCATCTCACGTACAGGTGAGCTGATTAAAA

WT     TTGCTTCAGATTTAGACATTATTCAAAAGGCTGGTGCTTGGTTCTCTTATAACGGTGAAAAAATTGGTCAGGGCTCTGAA
SHMAPR TTGCTTCAGATTTAGACATTATTCAAAAGGCTGGTGCTTGGTTCTCTTATAACGGTGAAAAAATTGGTCAGGGCTCTGAA

-continued

```
WT     AATGCCAAGAGATATTTGGCTGATCACCCAGAGCTGTTTGATGAGATTGACCATAAGGTGCGTGTTAAATTTGGCTTGCT
SHMAPR AATGCCAAGAGATATTTGGCTGATCACCCAGAGCTGTTTGATGAGATTGACCATAAGGTGCGTGTTAAATTTGGCTTGCT

WT     TGAAGATACTGAGGAAAGTGCAGCTGCAGATACAGTTGCAGCCAAAGCAGATGAGTTGGTTTTAGAGCTAGACGATGCCA
SHMAPR TGAAGATACTGAGGAAAGTGCAGCTGCAGATACAGTTGCAGCCAAAGCAGATGAGTTGGTTTTAGAGCTAGACGATGCCA

WT     TTGAAATTGAGGATTAG
SHMAPR TTGAAATTGAGGATTAG
```

The EcoRV restriction site used-
to generate the deletion construct is shown in italics.

The invention claimed is:

1. The *S. equi* strain SHMAPR deposited under accession number 13412 with the NCTC.

2. The deposited strain of claim 1 in a microbiological pure bacterial culture.

* * * * *

SEQUENCE LISTING

<160> NUMBER OF SEQ ID NOS: 38

<210> SEQ ID NO 1
<211> LENGTH: 165
<212> TYPE: DNA
<213> ORGANISM: Streptococcus equi

<400> SEQUENCE: 1
atgttacaat ttgcttcaaa tattttagct actagtgtag cagaaacaac tcaagttgct 60
cctggtggtt gctgctgttg ctgttcttgt tgttgctgcg tctcagcttc atggggcaat 120
actaccataa acaacaatta tggtgcagct gagccaaaag cgtaa 165

<210> SEQ ID NO 2
<211> LENGTH: 39
<212> TYPE: DNA
<213> ORGANISM: Artificial sequence
<220> FEATURE:
<223> OTHER INFORMATION: Synthetic sequence: S. equi strain SHMPAR, sagA deletion

<400> SEQUENCE: 2
atgttacaat ttgctaagct tgctgagcca aaagcgtaa 39

<210> SEQ ID NO 3
<211> LENGTH: 1254
<212> TYPE: DNA
<213> ORGANISM: Streptococcus equi

<400> SEQUENCE: 3
atgagaacat taaaaaacct cataactgtt gtggccttta gtatttttttg ggtactgttg 60 atttacgtca atgtttatct ctttggtgct aaaggaagct tgtcaattta tggctttttg 120
ctgatagctt atctattagt caaaatgtcc ttatcttttt tttacaagcc atttaaggga 180
agggctgggc aatataaggt tgcagccatt attccctctt ataacgaaga cgctgagtca 240
ttgctagaga ccttaaaaag tgttcagcag caaacctatc ccctagcaga aatttatgtt 300
gttgacgatg gaagtgctga tgagacaggt attaagcgca ttgaagacta tgtgcgtgac 360
actggtgacc tatcaagcaa tgtcattgtt catcggtcag agaaaaatca aggaaagcgt 420
catgcacagg cctgggcctt tgaaagatca gacgctgatg tctttttgac cgttgactca 480
gatacttata tctaccctga tgctttagag gagctgttaa agacctttaa tgacccaact 540
gtttttgctg cgacgggtca ccttaatgtc agaaatagac aaaccaatct cttaacacgc 600
ttgacagata ttcgctatga taatgctttt ggcgttgaac gagctgccca atcagttacg 660
ggtaatatcc ttgtttgctc aggcccactt agcgtttaca gacgcgaggt ggttgttcct 720
aatatagaca gatacatcaa ccagaccttc ctgggtattc ctgtaagtat cggtgatgac 780

-continued aggtgcttga ccaactatgc aactgattta ggaaagactg tttatcaatc cactgctaaa 840
tgtattacag atgttcctga caagatgtct acttacttga agcagcaaaa ccgctggaac 900
aagtccttct ttagagagtc cattatttct gttaagaaaa tcatgaacaa tccttttgta 960
gccctatgga ccatacttga ggtgtctatg tttatgatgc ttgtttattc tgtggtggat 1020
ttctttgtag gcaatgtcag agaatttgat tggctcaggg ttttagcctt tctggtgatt 1080
atcttcattg ttgctctttg tcggaacatt cattacatgc ttaagcaccc gctgtccttc 1140
ttgttatctc cgttttatgg ggtgctgcat ttgtttgtcc tacagccctt gaaattgtat 1200
tctcttttta ctattagaaa tgctgactgg ggaacacgta aaaaattatt ataa 1254

<210> SEQ ID NO 4
<211> LENGTH: 659
<212> TYPE: DNA
<213> ORGANISM: Artificial sequence
<220> FEATURE:
<223> OTHER INFORMATION: Synthetic sequence: S. equi strain SHMPAR, hasA deletion

<400> SEQUENCE: 4
atgagaacat taaaaaacct cataactgtt gtggccttta gtattttttg ggtactgttg 60
atttacgtca atgtttatct ctttggtgct aaaggaagct tgtcaattta tggctttttg 120
ctgatagctt atctattagt caaaatgtcc ttatcttttt tttacaagcc atttaaggga 180
agggctgggc aatataaggt tgcagccatt attccctctt ataacgaaga cgctgagtca 240
ttgctagaga ccttaaaaag tgttcagcag caaacctatc cctagcagaa aatgatatct 300
ggaacaagtc cttctttaga gagtccatta tttctgttaa gaaaatcatg aacaatcctt 360
ttgtagccct atggaccata cttgaggtgt ctatgtttat gatgcttgtt tattctgtgg 420
tggatttctt tgtaggcaat gtcagagaat ttgattggct cagggtttta gcctttctgg 480
tgattatctt cattgttgct ctttgtcgga acattcatta catgcttaag cacccgctgt 540
ccttcttgtt atctccgttt tatggggtgc tgcatttgtt tgtcctacag cccttgaaat 600
tgtattctct ttttactatt agaaatgctg actggggaac acgtaaaaaa ttattataa 659

<210> SEQ ID NO 5
<211> LENGTH: 1605
<212> TYPE: DNA
<213> ORGANISM: Streptococcus equi

<400> SEQUENCE: 5
atgtttttga gaaataacaa gcaaaaattt agcatcagaa aactaagtgc cggtgcagca 60
tcagtattag ttgcaacaag tgtgttggga gggacaactg taaaagcgaa ctctgaggtt 120
agtcgtacgg cgactccaag attatcgcgt gatttaaaaa atagattaag cgaaatagcc 180
ataagtagag atgcctcatc agcccaaaaa gttcgaaatc ttctaaaagg cgcctctgtt 240
ggggatttac aggcattatt gagaggtctt gattcagcaa gggctgcgta tggtagagat 300
gattattaca atttattggt gcacctttca tcgatgttaa atgataaacc tgatggggat 360
agaagacaat taagtttggc ttcattactt gtagatgaaa ttgaaaagcg gattgctgat 420
ggagatagtt atgcaaaact tcttgaggct aaacttgcag ctattaaatc tcaacaagaa 480
atgcttagag aaagagattc ccaacttcga aatctagaga aggaaaaaga acaagaacta 540
caaaaagcta aagatgagcg tcaagctctt accgaatcat tcaacaaaac tttatcaaga 600
tcaacaaaag agtataataa actaaaaaca gaacttgcaa aagaaaaaga aaaagcagct 660
aagatgacta aggaattagc agataagcta agcaatgctg aagcaagtcg tgataaagcc 720

-continued

```
tttgcagtat caaaagattt agcagataaa ctaagtagtg ctgaagcaag tcgtgataaa    780

gcttttgcag tatcaaaaga tttagcagat aaattggcag ctaaaacagc agaagctgaa    840

aagttaatgg aaaacgttgg tagtctagac cgcttggtag agtctgcaaa acgtgaaatg    900

gctcaaaaat tagcagaaat tgatcaatta actgctgata aggctaaggc tgatgcagag    960

cttgcagctg caaatgacac cattgcatca cttcaaacag agctagaaaa agctaagaca   1020

gagcttgctg tttcagagcg tttgattgaa tcaggcaaac gtgaaattgc tgagctacaa   1080

aaacaaaaag atgcttctga taaggcttta gtagaatcac aagctaatgt agcagagctt   1140

gaaaaacaaa aagcagcatc agatgctaag gtagcagagc ttgaaaaaga agttgaagct   1200

gctaaagctg aggttgcaga tcttaaagta caattagcta agaaagaaga agagcttgaa   1260

gccgttaaga aggaaaaaga agcgcttgaa gctaagattg aagagctcaa aaaagctcat   1320

gctgaggaac tttcaaaact taaagaaatg cttgagaaga aagaccatgc aaatgcagat   1380

cttcaagcag aaatcaatcg cttgaagcaa gagctagctg acaggattaa gtcattgtca   1440

caaggtggtc gtgcttcaca aacaaaccca ggcactacaa ctgctaaagc aggtcaattg   1500

ccatctactg gtgagtctgc taacccattc ttcactattg cagctcttac tgtcatcgct   1560

ggtgctggta tggctgtggt gtctcctaaa cgcaaagaaa actaa                   1605
```

<210> SEQ ID NO 6
<211> LENGTH: 795
<212> TYPE: DNA
<213> ORGANISM: Artificial sequence
<220> FEATURE:
<223> OTHER INFORMATION: Synthetic sequence: S. equi strain SHMPAR, seM deletion

<400> SEQUENCE: 6

```
atgtttttga gaaataacaa gcaaaaattt agcatcagaa aactaagtgc cggtgcagca     60

tcagtattag ttgcaacaag tgtgttggga gggacaactg taaaagcgaa ctctgaggtt    120

agtcgtacgg cgactccaag attatcgcgt gatttaaaaa atagattaag cgaaatagcc    180

ataagtagag atgcctcatc agcccaaaaa gttcgaaatc ttctaaaagg cgcctctgtt    240

ggggatttac aggcattatt gagaggtctt gattcagcaa gggctgcgta tggtagagat    300

gattattaca atttattggt gcaccttcca tcgatgtaaa atgatatctg agatgctaag    360

gtagcagagc ttgaaaaaga agttgaagct gctaaagctg aggttgcaga tcttaaagta    420

caattagcta agaaagaaga agagcttgaa gccgttaaga aggaaaaaga agcgcttgaa    480

gctaagattg aagagctcaa aaaagctcat gctgaggaac tttcaaaact taaagaaatg    540

cttgagaaga aagaccatgc aaatgcagat cttcaagcag aaatcaatcg cttgaagcaa    600

gagctagctg acaggattaa gtcattgtca caaggtggtc gtgcttcaca aacaaaccca    660

ggcactacaa ctgctaaagc aggtcaattg ccatctactg gtgagtctgc taacccattc    720

ttcactattg cagctcttac tgtcatcgct ggtgctggta tggctgtggt gtctcctaaa    780

cgcaaagaaa actaa                                                     795
```

<210> SEQ ID NO 7
<211> LENGTH: 1083
<212> TYPE: DNA
<213> ORGANISM: Streptococcus equi

<400> SEQUENCE: 7

```
atgacacaaa cacttcaggt taagtctcgt atcaatgact atccgattat ctttacagac     60
```

gatatttttc agccgctgaa tcaatttctt gctgaaaaag gagacgtcaa gctattattt 120
atcactgatc aaacggtatt tgatttatac cagcctttat ttagacgttt tcaacaggat 180
tacgatagtt accttcatat tgctgctcca gggggcaat ctaagtctct agaggaggtt 240
agtcggattt acgatcgact gattagggct aatttttcta aaaaggacgt cattgttact 300
gttggaggag gggtgattgg agatcttggg ggatttgttg cggcaacctt ttaccgcggg 360
atttcctacg ttcagattcc aacaacctta cttagtcagg tagacagcag cattggtggt 420
aaggttgggg ttcactttaa gggcttgacc aatatgatag gcagtatcta ccctccaaac 480
cagattatcg tgtcagccaa gtttttagac acgctttctg aaagagaatt tgcctgcggc 540
atcagcgaaa tgattaaaat tggttttatt catgatcgca agctctttca acagctccta 600
gccttcccca aggaccgcaa tcaagagcag ctcaggcaaa tgatttttca agcgatttgc 660
cataaaaaaa gagtggttga aaaggatgaa tttgaaggca atctccgcat gtccttaaat 720
ttcgggcata cgctagggca tgcgattgaa gccttatgcc atcacgagct ttacaggcat 780
ggtgaggcta ttgcgattgg catggtcttt gaggccaagc tggccgtcca gcagcagcta 840
ttgagccaac aggatttaga ggcattacag gctgcctttg aggcttatca gctacctacc 900
acacttgagg ctaagtcaat gacagccgaa gccttgatga ctgtttttaa aacagataag 960
aaaaattctg gtcagcatat tgtcctcatt ttgccaacga caaaaggcta tgtaagcttt 1020
cctattgcta agcatgacag tcgcctgctg gattggctaa gaagcctgct agatatcgcc 1080
tga 1083

<210> SEQ ID NO 8
<211> LENGTH: 56
<212> TYPE: DNA
<213> ORGANISM: Artificial sequence
<220> FEATURE:
<223> OTHER INFORMATION: Synthetic sequence: S. equi strain SHMPAR, aroA deletion

<400> SEQUENCE: 8
atgacacaaa cacttcaggt taagtctcgt atcaatgact atccgatatc gcctga 56

<210> SEQ ID NO 9
<211> LENGTH: 1413
<212> TYPE: DNA
<213> ORGANISM: Streptococcus equi

<400> SEQUENCE: 9
atgatatcag ggatcaagac agttacgtcc gatatgtcaa gcaaaacaaa taatcactgc 60
ctagataaat cagaaattgc tagggttatg cttgattatc ctgataagca gataagtaga 120
tttgacatag gaggggtcat gttattaatt aaaaatgggc gtgtgatgga tccaaaatca 180
cagctagatc aggtggcaga tgtcttaatt gataatggaa ggattttacg gattgctcca 240
gacattgagc atgatgaggt agagcagatc gatgccagtg gacttgttgt tgctcctggt 300
ttagtggata ttcatgttca ttttagagag ccgggtcaaa cgcacaagga ggacattcat 360
acaggtgctc tggcagcagc tgctggtggg gtgacaacag tagtcatgat ggcaaacacc 420
aatcctgtta tatcagatac ggaaacctta caggctgttc tagcaagtgc tgctaaagaa 480
aaaattaaca tttataccaa tgctagtgtg accaagcggt tcaatggcca agagctaaca 540
gactttaaag cgctcttagc agctggtgcg gtcagttttt ctgatgatgg cattccttta 600
gagagctcca aggtcttaaa ggaagcattg gatttggcta aggccaacaa gaccttcatt 660
gccctgcatg aggaggatcc ccaattaaac ggtgtccttg gcttcaatga gcatatcgct 720

```
aaggatcatt ttcatttttg tggcgctact ggtgtggcag aatatagtat gattgccaga    780

gatgtgatga ttgcctatga tcgacaagct catgttcata ttcaacattt atctaaggct    840

gagtctgtta aggtagttgc ctttgctcag cagttaggtg ccaaggtcac agccgaggca    900

acaccgcagc atttttctaa aacagaagac cttttacggc ttgcaggggc aaatgccaag    960

atgaatccgc ctctaagaac agaacaagat agattagcag ttattgaggg gctcaaatca   1020

ggtgtcatag ctattattgc aacggatcat gcaccacatc atcgtgatga aaaggccgtt   1080

gctgatctga ccaaggcacc atctggaatg accggcttag aaacctcatt gtcattaggc   1140

ctgacaaatc ttgtggagcc gagccatctt tcattgatgg cgttattaga gaaaatgacc   1200

attaatccag cctcactata tagctttgat gctggttatt tggctgagtc tggccctgct   1260

gatcttgtta tttttgctga caaggaggag cgtttggtaa cagaagcctt tgcttcaaag   1320

gctagtaatt caccttttat tggcgaaacc ctaaagggag ttgtgaaata caccattgct   1380

aagggacaaa ttgtttatca ggcagacaac taa                                1413
```

<210> SEQ ID NO 10
<211> LENGTH: 328
<212> TYPE: DNA
<213> ORGANISM: Artificial sequence
<220> FEATURE:
<223> OTHER INFORMATION: Synthetic sequence: S. equi strain SHMPAR, pyrC deletion

<400> SEQUENCE: 10

```
atgatatcag ggatcaagac agttacgtcc gatatgtcaa gcaaaacaaa taatcactgc     60

ctagataaat cagaaattgc tagggttatg cttgattatc ctgataagca gataagtaga    120

tttgacatag gaggggtcat gttattaatt aaaaatgggc gtgtgatgga tccaaaatca    180

cagctagatc aggtggcaag cttagcgttt ggtaacagaa gcctttgctt caaaggctag    240

taattcacct tttattggcg aaaccctaaa gggagttgtg aaatacacca ttgctaaggg    300

acaaattgtt tatcaggcag acaactaa                                       328
```

<210> SEQ ID NO 11
<211> LENGTH: 1137
<212> TYPE: DNA
<213> ORGANISM: Streptococcus equi

<400> SEQUENCE: 11

```
ttggcaaaaa aagttaaaaa aaatgaagaa atcaccaaaa aatttggtga tgaacgtcgt     60

aaagcacttg atgatgcgtt aaagaacatc gaaaaagatt ttggtaaggg tgcggttatg    120

cgccttggtg agcgtgcaga gcaaaaggtt caggtgatga gttcaggcag tcttgcttta    180

gacattgcgc ttggagcagg tggctatcct aaagggcgta ttattgaaat ctatggacca    240

gagtcttctg gtaaaacaac agttgccctg catgcagtag cgcaggctca aaaagaaggt    300

ggtattgcag ccttcattga tgcggagcat gccttggacc ctgcttatgc tgcggcgctg    360

ggtgttaata ttgatgagct gcttttgtca cagccggatt ctggtgagca aggacttgag    420

atagcaggta aactgattga ttctggtgct gttgatttgg ttgttgtcga ctctgttgca    480

gctctagtgc ctcgtgctga gattgatggt gatattggtg ataaccatgt tggcttgcag    540

gctcgtatga tgagtcaggc gatgcgtaag ctttcagcct caatcaataa aaccaagaca    600

attgcgatct ttattaacca gctgcgtgaa aaggtagggg ttatgtttgg taatccagag    660

acgacaccag gtggtcgtgc tttgaaattc tatgcctctg tccgtctgga tgttcgtgga    720
```

acaacacaaa taaaaggaac tggagatcaa aaagacagta gtattggtaa ggaaaccaag 780
attaaggttg ttaagaataa ggttgctccg ccatttaagg tggctgaggt tgaaatcatg 840
tatggagaag gcatctcacg tacaggtgag ctgattaaaa ttgcttcaga tttagacatt 900
attcaaaagg ctggtgcttg gttctcttat aacggtgaaa aaattggtca gggctctgaa 960
aatgccaaga gatatttggc tgatcaccca gagctgtttg atgagattga ccataaggtg 1020
cgtgttaaat ttggcttgct tgaagatact gaggaaagtg cagctgcaga tacagttgca 1080
gccaaagcag atgagttggt tttagagcta gacgatgcca ttgaaattga ggattag 1137

<210> SEQ ID NO 12
<211> LENGTH: 611
<212> TYPE: DNA
<213> ORGANISM: Artificial sequence
<220> FEATURE:
<223> OTHER INFORMATION: Synthetic sequence: S. equi strain SHMPAR, recA deletion

<400> SEQUENCE: 12
ttggcaaaaa aagttaaaaa aaatgaagaa atcaccaaaa aatttggtga tgaacgtcgt 60
aaagcacttg atgatgcgtt aaagaacatc gaaaaagatt ttggtaaggg tgcggttatg 120
cgccttggtg agcgtgcaga gcaaaaggtt caggtgatga gttcaggcag tcttgcttta 180
gacattgcgc ttggagcagg tggctatcct aaagggcgta ttattgaaat ctatggacca 240
gagtcttctg gtaaaacaac agttgccctg catgcagtag cgcaggctca aaaagaaggt 300
ggtattgcag ccttgatatc gaaggcatct cacgtacagg tgagctgatt aaaattgctt 360
cagatttaga cattattcaa aaggctggtg cttggttctc ttataacggt gaaaaaattg 420
gtcagggctc tgaaaatgcc aagagatatt tggctgatca cccagagctg tttgatgaga 480
ttgaccataa ggtgcgtgtt aaatttggct tgcttgaaga tactgaggaa agtgcagctg 540
cagatacagt tgcagccaaa gcagatgagt tggttttaga gctagacgat gccattgaaa 600
ttgaggatta g 611

<210> SEQ ID NO 13
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 13
ggggaattct gaggtactag ccatctgtc 29

<210> SEQ ID NO 14
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 14
gggaagctta gcaaattgta acataatgct tacc 34

<210> SEQ ID NO 15
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 15

-continued

```
gggaagcttg ctgagccaaa agcgtaaac                                    29


<210> SEQ ID NO 16
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 16

ggggtcgaca aaactcagcc acactggtc                                    29


<210> SEQ ID NO 17
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 17

ggggaattca agggaagggc tgggcaatat aagg                              34


<210> SEQ ID NO 18
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 18

ggggatatca tttctgacat taaggtgacc cgtc                              34


<210> SEQ ID NO 19
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 19

ggggatatct ggaacaagtc cttctttaga gag                               33


<210> SEQ ID NO 20
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 20

ggggtcgaca gggctgtagg acaaacaaat gcag                              34


<210> SEQ ID NO 21
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 21

ggggaattca tgttttagag aaataacaag c                                 31


<210> SEQ ID NO 22
<211> LENGTH: 30
<212> TYPE: DNA
<213> ORGANISM: Artificial sequence
```

<220> FEATURE:
<223> OTHER INFORMATION: Synthetic sequence: Primer

<400> SEQUENCE: 22
ggggatatca ttttacatcg atgaaaggtg 30

<210> SEQ ID NO 23
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 23
ggggatatct gagatgctaa ggtagcagag c 31

<210> SEQ ID NO 24
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 24
ggggtcgacg ttttctttgc gtttaggaga cacc 34

<210> SEQ ID NO 25
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 25
gacgaattct gtctgaaagg cagctagag 29

<210> SEQ ID NO 26
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 26
gacgacgata tcggatagtc attgatacga gac 33

<210> SEQ ID NO 27
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 27
gctagatatc gcctgagaag gct 23

<210> SEQ ID NO 28
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 28
gacgacgtcg actggtaaga cctggacaac ag 32

<210> SEQ ID NO 29
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 29
acacctgatc ttgccttgtc 20

<210> SEQ ID NO 30
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 30
gacgaattcg cagcagatat tggagtaagg 30

<210> SEQ ID NO 31
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 31
gacgacaagc ttgccacctg atctagctgt gat 33

<210> SEQ ID NO 32
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 32
gacgacaagc ttagcgtttg gtaacagaag cc 32

<210> SEQ ID NO 33
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 33
gacgacgtcg actacgtttc ggattcttgg gc 32

<210> SEQ ID NO 34
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 34
ggcaggctat tatggctaag 20

<210> SEQ ID NO 35
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 35

-continued

```
gacgacgaat tcttattgct tgctagtcag cc                                32


<210> SEQ ID NO 36
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 36

gacgacgata tcaaggctgc aataccacct tc                                32


<210> SEQ ID NO 37
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 37

gacgacgata tcgaaggcat ctcacgtaca gg                                32


<210> SEQ ID NO 38
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 38

gacgacgtcg acttgacgat cgctgttaag cc                                32
```